(12) United States Patent
Wooley et al.

(10) Patent No.: US 9,339,387 B2
(45) Date of Patent: May 17, 2016

(54) SYNTHETIC BONE GRAFTS CONSTRUCTED FROM CARBON FOAM MATERIALS

(75) Inventors: Paul Hastings Wooley, Wichita, KS (US); Haiying Yu, Wichita, KS (US)

(73) Assignee: CIBOR, INC., Wichita, KS (US)

( * ) Notice: Subject to any disclaimer, the term of this patent is extended or adjusted under 35 U.S.C. 154(b) by 242 days.

(21) Appl. No.: 13/272,793

(22) Filed: Oct. 13, 2011

(65) Prior Publication Data

US 2012/0095558 A1   Apr. 19, 2012

Related U.S. Application Data

(60) Provisional application No. 61/392,789, filed on Oct. 13, 2010.

(51) Int. Cl.
| | | |
|---|---|---|
| A61F 2/28 | (2006.01) |
| A61L 27/08 | (2006.01) |
| A61L 27/32 | (2006.01) |
| A61L 27/54 | (2006.01) |
| A61L 27/56 | (2006.01) |
| A61F 2/30 | (2006.01) |

(52) U.S. Cl.
CPC . *A61F 2/28* (2013.01); *A61L 27/08* (2013.01); *A61L 27/32* (2013.01); *A61L 27/54* (2013.01); *A61L 27/56* (2013.01); *A61F 2002/2835* (2013.01); *A61F 2002/30011* (2013.01); *A61F 2002/30062* (2013.01); *A61F 2002/3092* (2013.01); *A61F 2310/0097* (2013.01); *A61F 2310/00161* (2013.01); *A61F 2310/00173* (2013.01); *A61F 2310/00796* (2013.01); *A61F 2310/00976* (2013.01); *A61L 2430/02* (2013.01)

(58) Field of Classification Search
None
See application file for complete search history.

(56) References Cited

U.S. PATENT DOCUMENTS 4,070,514 A * 1/1978 Eatherly et al. ............. 428/64.1
4,978,358 A   12/1990 Bobyn (Continued)

FOREIGN PATENT DOCUMENTS

EP           35593  A2 *  9/1981  ............. A61K 9/20

OTHER PUBLICATIONS

Turgut, "Pore structure engineering for carbon foams as possible bone implant material," J. Biomed Mater Res A, Jun. 1, 2008;85(3):588-96.*
"Reticulated Vitreous Carbon", ERG Materials and Aerospace Corporation website. Jun. 26, 2001.*
Pec et al. "Reticulated Vitreous Carbon: A Useful Material for Cell Adhesion and Tissue Invasion", European Cells and Materials, vol. 20, 2010, pp. 282-294.*
Aoki et al. "A Thin Caron-Fiber Web as a Scaffold for Bone-Tissue Regeneration", Small, 2009, 5, No. 13, 1540-1546.*

(Continued)

*Primary Examiner* — Thomas J Sweet
*Assistant Examiner* — Megan Wolf
(74) *Attorney, Agent, or Firm* — Hovey Williams LLP

(57) ABSTRACT

A porous, self-sustaining body useful as a scaffold for bone grafting is provided. The scaffold comprises a carbonaceous matrix comprising a continuous phase having a surface and defining a plurality of open spaces throughout the matrix. The internal and external surfaces of the matrix are coated with a layer or film selected from the group consisting of osteogenic materials, therapeutic agents, and combinations thereof. The porous body comprises organic materials and is substantially free of metals. Methods of making and using the porous self-sustaining body are also provided, along with kits for facilitating the same.

26 Claims, 17 Drawing Sheets
(7 of 17 Drawing Sheet(s) Filed in Color)

(56) References Cited

U.S. PATENT DOCUMENTS

| | | | |
|---|---|---|---|
| 5,282,861 | A | 2/1994 | Kaplan |
| 5,888,469 | A * | 3/1999 | Stiller et al. ............... 423/445 R |
| 6,103,149 | A | 8/2000 | Stankiewicz |
| 6,187,047 | B1 | 2/2001 | Kwan et al. |
| 6,846,327 | B2 * | 1/2005 | Khandkar et al. .......... 623/16.11 |
| 7,401,643 | B2 * | 7/2008 | Queheillalt et al. ...... 165/104.21 |
| 7,959,941 | B2 | 6/2011 | Knaack et al. |
| 7,964,206 | B2 | 6/2011 | Suokas et al. |
| 7,968,026 | B1 | 6/2011 | Teoh et al. |
| 7,968,111 | B2 | 6/2011 | Pavesio et al. |
| 8,025,896 | B2 | 9/2011 | Malaviya et al. |
| 2004/0138754 | A1 * | 7/2004 | Lang et al. ................. 623/20.14 |
| 2005/0079201 | A1 * | 4/2005 | Rathenow et al. ............. 424/424 |
| 2006/0073089 | A1 * | 4/2006 | Ajayan et al. .............. 423/447.2 |
| 2006/0188542 | A1 | 8/2006 | Bobyn et al. |
| 2006/0271201 | A1 | 11/2006 | Kumar et al. |
| 2008/0206297 | A1 | 8/2008 | Roeder et al. |
| 2009/0248047 | A1 * | 10/2009 | Marrs et al. .................... 606/151 |
| 2010/0255053 | A1 | 10/2010 | Savage-Erickson |

OTHER PUBLICATIONS

ERG Materials and Aerospace Corporation, Duocel® RVC foam brochure, "Reticulated Vitreous Carbon: A New Form of Carbon", https://web.archive.org/web/19980215012143/http:/www.ergaerospace.com/lit.htm acessed Apr. 14, 2015.*

Translation of EP 35593 A2, retrieved from Espacenet on Apr. 16, 2015.*

International Search Report and Written Opinion dated May 23, 2012, in corresponding PCT/US2011/056155 filed on Oct. 13, 2011.

Fauber, "Infuse cited in patients' painful bone overgrowth," JSOnline, Jun. 27, 2011, http://www.jsonline.com/watchdog/watchdogreports/124630959.html.

Medtronic Infuse® Bone Graft + LT-Cage® Lumbar Tapered Fusion Device Fact Sheet, 2011, http://wwwp.medtronic.com.

Turgut, "Pore structure engineering for carbon foams as possible bone implant material," J. Biomed Mater Res A, Jun. 1, 2008;85(3):588-96, PubMed abstract only, www.ncbi.nlm.nih.gov/pubmed/17806113.

* cited by examiner

A. One Day Post-op       B. Six weeks Post-op

US 9,339,387 B2

SYNTHETIC BONE GRAFTS CONSTRUCTED FROM CARBON FOAM MATERIALS

CROSS-REFERENCE TO RELATED APPLICATIONS

The present application claims the priority benefit of U.S. Provisional Patent Application Ser. No. 61/392,789, filed Oct. 13, 2010, entitled Synthetic Bone Grafts Constructed from Carbon Foam Composite Materials, incorporated by reference in its entirety herein.

BACKGROUND OF THE INVENTION

1. Field of the Invention

The present invention relates to organic bone void fillers comprising carbonaceous material for repairing bone voids, and particularly structural bone voids.

2. Description of Related Art

Bone is a regenerative tissue that can sometimes effectively repair fracture damage and small voids, but trauma that results in the loss of a large bone segment requires the use of a bone void filler to bridge the gap between bone segments. Bone void fillers are natural or synthetic materials placed into the bone defect to assist in bone regeneration and provide a three-dimensional structure to which bone tissue and cells can attach or be transplanted to regrow and repair damaged bone segments. Autologous, allogeneic, or xenogeneic bone grafts can be used for this purpose. However, in major traumatic injury, there is usually insufficient autologous bone available as a void filler. In addition, harvesting of the graft from the donor site for bone autografts causes a secondary trauma to the patient. This is avoided by the use of allografts and xenografts; however, these bone grafts require the use of immunosuppressives to avoid implant rejection by the patient, can transmit viruses, and have a relatively high failure rate.

Synthetic bone void fillers such as demineralized bone matrix or polymethylmethacrylate have also been employed. However, current bone fillers are generally intended for use only in voids that are not intrinsic to the stability of the bone structure, since most available materials possess insufficient strength and ultimate stress capabilities for such applications. Implants used for bone voids intrinsic to structural stability of the bone often involve permanent implant materials formed from metal, polymers, or composites; however, these types of implants are prone to corrosion and leaching. In addition, all metals, most ceramics, and many polymers are not bioresorbable, and cannot be replaced by the patient's own bone tissue. Thus, there remains a need in the art for a sufficiently strong temporary bone void filler suitable for use in load-bearing applications, that provides a template for osteogenesis that gradually degrades and is resorbed as it is replaced by bone tissue, until bone generation/regeneration is complete.

SUMMARY OF THE INVENTION

The present invention is broadly concerned with a porous, self-sustaining body useful as a scaffold for bone grafting. The porous, self-sustaining body comprises a carbonaceous matrix comprising a continuous phase having a surface and defining a plurality of open spaces throughout the matrix; and a coating adjacent the continuous phase surface of the matrix. The coating is selected from the group consisting of osteogenic materials, therapeutic agents, and combinations thereof. The porous body is substantially free of metals, and preferably other inorganic materials. In one or more embodiments, the matrix is formed of a carbonaceous material selected from the group consisting of carbon foam, graphitic foam, and combinations thereof.

In another aspect, there is provided a method of making a porous, self-sustaining body useful as a scaffold for bone grafting. The method comprises providing a carbonaceous matrix comprising a continuous phase having a surface and defining a plurality of open spaces throughout the matrix; and forming a coating adjacent the continuous phase surface of the matrix. The coating is selected from the group consisting of osteogenic materials, therapeutic agents, and combinations thereof. The porous body is substantially free of metals.

The invention is also concerned with a method of repairing or replacing in a subject a bone void having a given size and shape. The method comprises providing a porous, self-sustaining body useful as a scaffold for bone grafting, shaping the porous body to fit the bone void size and shape; and fitting the porous body into the bone void. The porous, self-sustaining body comprises a carbonaceous matrix comprising a continuous phase having a surface and defining a plurality of open spaces throughout the matrix; and a coating adjacent the continuous phase surface of the matrix. The coating is selected from the group consisting of osteogenic materials, therapeutic agents, and combinations thereof. The porous body is substantially free of metals.

A kit for use in repairing or replacing in a subject a bone void having a given size and shape is also provided. The kit comprises a porous, self-sustaining body useful as a scaffold for bone grafting, and instructions for the implantation thereof into the subject. The porous, self-sustaining body comprises a carbonaceous matrix comprising a continuous phase having a surface and defining a plurality of open spaces throughout the matrix; and a coating adjacent the continuous phase surface of the matrix. The coating is selected from the group consisting of osteogenic materials, therapeutic agents, and combinations thereof. The porous body is substantially free of metals. Additional details about the invention are described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The present invention is concerned with bone void fillers or implants (i.e., scaffolds) for bone grafting to repair, restore, or replace voids, defects, or gaps in bone resulting from, for example, fractures, breaks, or other trauma, defects, surgical resection, disease, or other damage to the bone, and permit bone tissue generation/regeneration. The inventive scaffolds are synthetic and avoid the drawbacks typically encountered with allogenic, autogenic, or xenogeneic bone graft materials. However, the inventive scaffolds are formed of organic materials with improved biocompatibility over existing scaffolds. Advantageously, the inventive bone void fillers and implants have mechanical properties similar to trabecular bone and can be used for weight-bearing bone voids, but as explained in more detail below, unlike metal, bone cement, or other permanent implants often used in such cases, the inventive implants are bioresorbable as the implant is infiltrated and replaced by new bone tissue.

Figure 1:
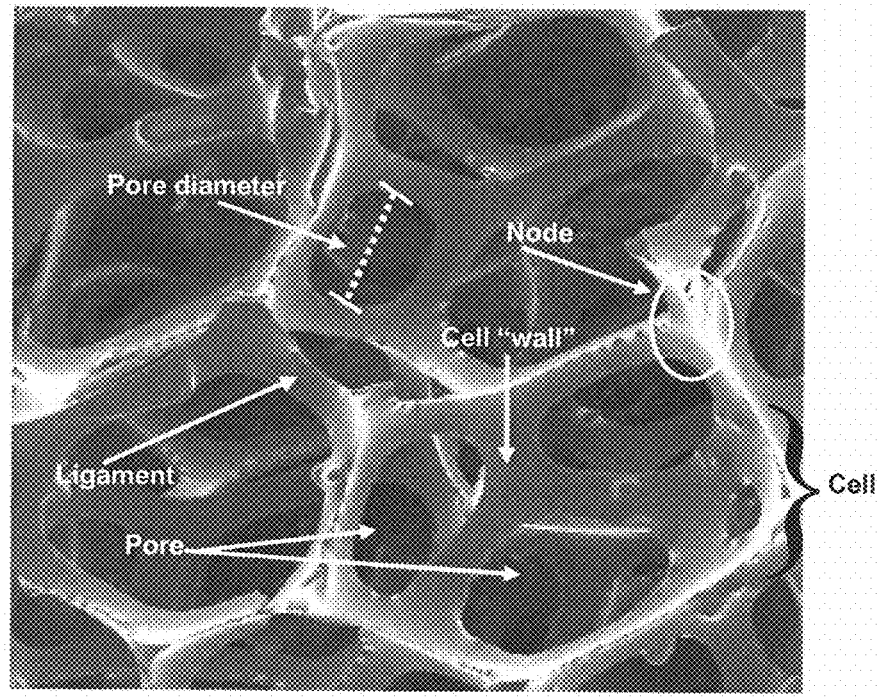
FIG. 1 is an SEM image of reticulated vitreous carbon (RVC) foam annotated to illustrate nodes, ligaments, and cells that make up the matrix microstructure.

In more detail, the invention provides an implantable porous self-sustaining body which serves as a scaffold for new bone tissue growth. The term "self-sustaining," as used herein means the body is substantially rigid and maintains its shape without an external support structure, and is not susceptible to deformation merely due to its own internal forces. Specific mechanical properties of the implant are discussed in more detail below. The porous body comprises a carbonaceous matrix characterized by a continuous phase having a surface and defining a plurality of open spaces (i.e., cavities, voids, and pores) throughout the matrix (i.e., internal and external open spaces). The continuous phase is formed of a carbonaceous material, and preferably consists essentially or even consists of the carbonaceous material. In one or more embodiments, the carbonaceous material is selected from the group consisting of carbon foam and/or graphite foam. Carbon and graphite foams are generally characterized by a three-dimensional bonding between carbon atoms ("nodes") to form cells, which are further interconnected via ligaments. The cell walls, nodes, and ligaments together create the interconnected network (i.e., continuous phase) of the matrix, which defines the open spaces of the matrix, with the pores being those open spaces or holes formed through the cell walls. Suitable carbon foams for use in the invention include, without limitation, pyrolytic carbon foams, vitreous carbon foams, and the like. For ease of reference, unless otherwise specified, the term "carbon foam" is used herein to include graphitic foams, although true (amorphous) carbon foams are particularly preferred for use in the invention. The carbonaceous matrix has an open cell structure, and more preferably is a reticulated carbon foam. FIG. 1 is an annotated SEM image of a reticulated carbon foam. Reticulated carbon foams have interconnected pores throughout the matrix which allow the passage of gas or fluid through the open spaces from one cell to the next, as opposed to closed cell structures in which the cells are totally enclosed by their walls and do not have interconnected openings. It will be appreciated that a combination of open and closed cell structures could also be present in the matrix; however, the matrix preferably primarily comprises an open cell structure. In other words, open cell matrices suitable for use in the invention may contain a small fraction of closed cells without departing from the intent of the invention.

Preferably the carbonaceous matrix has an average (median) pore diameter of at least about 50 μm, more preferably from about 80 to about 400 μm, and even more preferably from about from about 150 to about 250 μm. Pore diameter can be measured using micrograph images of the matrix, according to known standards in the art, as illustrated in FIG. 1. The matrix preferably has a porosity factor of at least about 80%, more preferably from about 75 to about 95%, and even more preferably from about 80 to about 90%. Porosity is the percentage of the volume of open or void space in the matrix as compared to the bulk volume of the matrix. It can be determined using fluid passage (or CT) techniques known in the art. The matrix preferably has a pore density (pores per linear inch or "PPI") of at least about 50, more preferably from about 75 to about 100, and even more preferably from about 80 to about 100, with about 80 being particularly preferred. Exemplary carbon foams for use in the invention are commercially available from various manufacturers, including, without limitation, ERG Aerospace Corp., Oakland, Calif. (DUOCEL® RVC 45, 60, 80, and 100 vitreous carbon foam); GrafTech International, Parma, Ohio (GRAFOAM® FPA-02, -05, -10, -20, and -35 graphitic foam); PocoGraphite, Inc., Decatur, Tex. (POCOfoam® graphitic foam); Koppers, Pittsburgh, Pa. (KFOAM® L1, L1a, and D1 graphitic foam); Touchstone Research Laboratory, Ltd., Triadelphia, W. Va. (CFOAM® 20, or 25); and Ultramet, Pacoima Calif. (RVC 65 PPI, 80 PPI, RVC with CVD materials, and RVC with integrally bonded coating). Methods for making carbon foams are also known in the art, including U.S. Pat. Nos. 6,103,149, 6,656,238, 6,656,239, and 6,749,652, incorporated by reference herein to the extent not inconsistent with the present disclosure.

The carbonaceous matrix of the porous body is preferably substantially of a uniform material throughout its three-dimensional structure. That is, the body preferably does not include any metals, plastics, composites, cements, or other inorganic structures or supports in, on, or through the body. As mentioned above, the matrix has self-supporting rigidity, with minimal bending, flexing, or compressing. Thus, the implant is particularly suited for load-bearing or other structural bone voids (i.e., voids intrinsic to the stability of the bone). The porous body preferably has an ultimate stress capability of at least about 0.2 MPa, more preferably from about 1 to about 15 MPa, even more preferably from about 2 to about 15 MPa, and most preferably from about 10 to about 15 MPa. Thus, the implant has the strength that will allow the repair of defects, including significant or large bone voids, previously untreatable by bone void fillers.

The porous body further comprises a coating adjacent the continuous phase surface of the matrix. Preferably at least about 75% of the continuous phase surface is covered by the coating, more preferably at least about 85%, and even more preferably from about 95% to about 100% of the continuous phase surface is covered by the coating, based upon the total available surface area taken as 100%. Thus, both the exterior and the interior surfaces of the matrix are preferably substantially covered by the coating. Solids, liquids, or combinations thereof can be used to form the coating. Solid coatings can be applied using plasma deposition techniques. Liquids (including gels or other fluids) can be applied by immersing or dipping the matrix into the liquid, spraying the liquid onto the matrix, or puddling the liquid onto the matrix and allowing it to permeate through the matrix pores. The coating can then be dried. Solids can also be dissolved or dispersed in a solvent system (e.g., distilled water) and applied as a liquid described above. Vacuum techniques can be used in conjunction with any of the above application methods to drive the coating material into the matrix. In any case, the matrix is "infused" with the coating material, such that the material is present as a coating, film, or monomolecular layer immobilized on and adjacent to the continuous surfaces throughout the interior and exterior of the matrix, but does not occlude the internal and/or external pores of the matrix. That is, after coating, less than about 10% of the pores are occluded by the coating material, preferably less than about 5%, and more preferably less than about 1% of the pores are occluded by the coating material. It will be appreciated that certain coating materials may have a tendency to occlude the pores of the matrix, or may be of a sufficient thickness as to significantly narrow the pore size; thus, it may be desirable to select a matrix having a higher initial porosity, or larger average pore diameter, such that the porosity or average pore diameter after coating remains within the target values disclosed herein.

Suitable coating materials are selected from the group consisting of osteogenic materials, therapeutic agents, and combinations thereof. It will be appreciated that a given coating material can be both osteogenic and therapeutic, and these categories are descriptive and not mutually exclusive. Osteogenic materials include both osteoinductive compositions and osteoconductive compositions. By comparison, osteoconductive compositions are ones which permit and even enhance bone growth over the surface of the material, and include allogenic or autogenic bone fragments, calcium phosphate, hydroxyapatite, coralline, sintered bone (Bio Oss®), porous polycaprolactone, and combinations thereof. Osteoinduction involves in-growth of bone tissue into (and not just over) the material. Therapeutic agents for use in the invention include small molecule drugs as well as biologics. Exemplary small molecule drugs include antibiotics (e.g., vancomycin, tobramycin, gentamicin), anti-inflammatories (e.g., COX-1, COX-2, steroidals), and anti-coagulants (e.g., conjugated heparins, warfarin). Exemplary biologics include proteins (e.g., collagen, albumin, bone morphogenetic proteins (BMPs), epithelial growth factors (EGF), recombinant human cytokines, hormones such as estrogen, etc.), lamellen, monoclonal antibodies, immunoglobulins, fusion proteins, cells (e.g., stem cells, osteoblasts, osteocytes, chondrocytes) and/or subcellular fractions, tissues, whole blood and/or blood components (e.g., plasma, fibrin, fibrinogen, vitronectin, platelet rich plasma, plasma components), enzymes, DNA, cDNA, gene therapy vectors, nucleic acid inhibitor, chemotherapeutics, and combinations thereof. It will be appreciated that many of the aforementioned biologics may also be considered osteoinductive materials. The carbonaceous matrix may also simply be coated with sterilized water, which has been shown to enhance bone growth.

The coating is immobilized on the carbonaceous matrix surfaces, but preferably is not covalently or otherwise chemically bonded thereto. Thus, the coating material is physically immobilized, relying instead on van der Waals or ionic-type attraction between the carbonaceous matrix surfaces and the coating material. This provides a significant advantage in that the osteogenic or therapeutic agents do not have to be chemically modified, and thus retain their full bioavailability when implanted into a patient, even though tightly bound to the matrix. Advantageously, the use of the coating in combination with the carbonaceous matrix permits not just in-growth of bone, but eventual through-growth of bone throughout the entirety of the matrix, as discussed in more detail below. The carbonaceous matrix is characterized by the ability to retain proteins loaded onto the matrix. More specifically, the porous body, when subjected to a protein elution test, as described herein, has the ability to retain at least about 30% of protein, more preferably at least about 40% of protein, and even more preferably at least about 50% of protein during formation of the coating. That is, when the matrix is infused with a solution containing a protein, such as BMP, at least about 30% of the protein from the free solution will be taken up and retained by the matrix (preferably at least about 40% and more preferably at least about 50%), based upon the total amount of protein in the solution taken as 100%. In other words, the protein content of the solution is decreased by at least about 30, 40, or preferably 50% after immersing the matrix into the solution.

Protein retention can be tested using a protein elution test as described herein. A significant component of this invention is the integration of biologically active cytokines or other biological materials within the carbon foam matrix, (present as coatings of the material) within anatomic locations requiring new bone/cartilage formation. The protein elution tests of this application are multi-partite and address important functional issues of productive contact between osteoinductive material and conductive carbon foam matrices, the degree of persistence of the binding interaction, the percentage of coating released to the surrounding milieu, and percentage retained in a biologically-active, bio-available form. An example of one such comprehensive analysis involves contacting selected foam materials with a cytokine solution of known concentration either by passage of the solution over the solid object or by low pressure vacuum loading. The concentration of the remaining wash solution following completion of a specified loading time is reevaluated by ELISA to determine the cytokine depletion and thus de facto transfer of cytokine to the carbon foam. Replicate loading studies using recombinant human BMP-2 (rhBMP) reliably yield depletion values of 50%, that is, simple contact between solute and carbon material yields transfer of 50% of the cytokine to the carbon foam from solution. Verification of this presumptive loading percentage can be validated using one of two methods: 1. Liquid phase ELISA of protein stripped from coated carbon foams with chaotropic agents (e.g., 4M guanidine hydrochloride) or reagents that interfere with ionic interaction (e.g., 5M NaCl; 0.5M glycine, NaOH, pH 10); or 2. Solid-phase ELISA of cytokine adsorbed to carbon matrix using BMP-2 antibody conjugated to biotin or chromogenic-generating enzyme providing quantification of the amount of BMP-2 adsorbed onto the material surface.

Bound BMPs (such as BMP-2 or other cytokines described herein) can also be evaluated by the criterion of biological activity by exposure of responding cells lines that are competent to respond to the adsorbed cytokine in question. That is, cells exposed to cytokine-coated matrices can readily be induced to develop novel phenotypes such as a bone-forming osteoblast that can be measured using a combination of enzymatic, molecular (real time PCR), and histochemical assays. We suggest that an important property of these combination devices is retention of biological activity (rather than migration away from) at the clinically-relevant site of implantation. Other embodiments of the cytokine-coated carbon foam materials having clinical utility in orthopaedic applications include surface modification of the carbon with blood proteins that can potentiate a reduction in the affinity with which the biologically active cytokine is retained. Orthopaedic applications that require rapid diffusion of a bioactive agent serving a chemotactic function with respect to mesenchymal cells embedded in surrounding tissues are in view in suggesting surface potential alterations.

In addition, the matrix has a remarkable ability to retain the coating in the matrix after implantation, drawing the components of the bone regeneration process into the matrix. This is particularly advantageous for the use of proteins such as BMP, which are retained by the matrix instead of being released into surrounding tissue, and avoids the formation of ectopic bone or unwanted bone overgrowth. After implantation, the porous body will preferably retain at least about 75%, more preferably at least about 80%, even more preferably at least about 90%, and most preferably at least about 95% of the immobilized protein, based upon the total initial protein content of the coating taken as 100%. This can be tested in vitro using a protein release test, as described in the working examples. Thus, when subjected to a protein release test for a period of about a week, implants according to the invention will have high retention and low release of bound protein. Thus, the rate of mineralization can be reliably controlled using the inventive implant, due to the linear relationship between the amount of osteogenic material (such as BMP) present in the implant, and the mineralization rate. Accordingly, a given amount of protein can be loaded onto the matrix before implantation to achieve a target level of mineralization, since very little protein is lost to surrounding tissue.

In one or more embodiments, the porous body consists essentially or even consists of the carbonaceous matrix and coating. That is, the porous body is substantially free of metals (such as titanium, titanium alloys, steel, tantalum, copper, silver, or cobalt chromium alloy), composites, plastics and polymers (such as polypropylene, polymethylmethacrylate, polyethylene, polyoxymethylene), and the like. The term "substantially free," as used herein, means that the porous body comprises less than about 1% by weight of a given substance, more preferably less than about 0.1% by weight of a given substance, and even more preferably about 0% by weight of a given substance, based upon the total weight of the body taken as 100% by weight.

In use, the implant is provided to a surgeon or other medical or clinical professional for placement and fixation in a bone void. The inventive implant can be used as a bone void filler for virtually any type of voids, defects, or gaps in bone, whether due to surgical resection, trauma, disease, etc. More specifically, the implant can be used as a bone graft scaffold for replacement and/or repair of entire or portions of bones, including long bones (e.g., femur, tibia, humerus, radius, ulna, etc.), calvarial defects, osteochondral defects, vertebrae, flat bones (e.g., scapula, pelvis) and the like. Thus, it will be appreciated that the implant may be of any variety of shapes and sizes including rods, bars, discs, ellipses, granules, etc. as well as amorphous shapes, to fit cavities or depressions in the bone, entirely resected bone sections (i.e., bridging two pieces of formally-intact bone), holes present through a bone, damaged or missing end sections, and the like. The implant can even be used in large bone voids, such as those due to significant trauma where the comminuted segment of the damage typically involves about 40% or more of the total length of the bone. The implant can be shaped using traditional machining or fabrication tools. A significant advantage of the inventive implant is that it can be readily shaped on-site by the surgeon or other technician using conventional surgical tools, such as scalpels, bone saws, drills, or Dremel®-type tools (e.g., grinders). Thus, the implant can be molded and contoured by the surgeon to fit the exact shape and size of the void and provide a precise interface with bone adjacent the void. This is a drastic improvement over many existing implants which are provided in a fixed size and shape, wherein the void itself must be altered to fit the implant, causing further trauma to the patient. It is envisioned that existing or future technology may even permit an extremely precise determination (imaging) of the shape and size of the void, followed by automated machine shaping of the implant to fit that void with extraordinary accuracy. In one or more embodiments, the implant is provided as a monolithic block (porous body) to the surgeon, preferably with instructions regarding shaping the block to fit the void and fixation of the implant in the void. Such a kit could also optionally include tools for shaping the implant, as well as appropriate tools and fasteners for fixing the filler in the void. It will be appreciated that the block can be of various sizes and shapes depending upon size of bone to be replaced. For example, for long bones and other large bone segments, length of the block could vary from about 6 to about 10 inches, and the width and thickness of the block could vary from about 0.5 to about 2 inches. The large "block" could also be in the shape of a rod having a length of about 6 to about 10 inches and a diameter of from about 0.5 to about 2 inches. Depending upon the size of the void, a portion of the large block could be cut off and molded to fit smaller voids. However, for larger bone voids, the entire block can be used to shape the implant. Alternatively, for smaller voids, the block can initially be provided to the surgeon as a smaller porous body to minimize the amount of shaping and sizing that must be done. The length of the smaller block could vary from about 1 to about 3 inches, and the width and thickness of the block could vary from about 0.5 to about 2 inches. The small "block" could also be in the shape of a rod having a length of about 1 to about 3 inches and a diameter of from about 0.5 to about 2 inches. Regardless, the implant can be shaped by cutting, carving, shaving, slicing, grinding, boring, and/or sanding the matrix material to the desired contours and size.

After the implant is shaped and sized to the bone void, it can be placed in the void and fixed using suitable techniques including pins, screws, friction-fit engagement, sutures, adhesives, the patients own skin or surrounding tissue, wires, cables, and/or combinations thereof. In one or more embodiments, the implant could also be placed in the void and (further) shaped or contoured, if necessary, before and/or after fixation. Advantageously, due to the biomechanical and biocompatibility properties of the implant being similar to or exceeding trabecular bone, the patient can return to weight-bearing activity much earlier than previous implants would have allowed, decreasing morbidity and enhancing the healing process. Preferably, the patient returns to reduced ambulatory weight-bearing (e.g., weight bearing as tolerated by patient) as soon as possible, more preferably within less than about 4 days after implantation, and even more preferably within less than about 2 days about after implantation. The patient is preferably able to begin toe tapping within about 24 hours after implantation. Those in the art will understand that toe tapping involves standing and moving with crutches, a walker, or other support, and carrying most of the weight on the good leg, while toe tapping with the ball of the foot on the repaired leg.

Once implanted, osteogenesis begins, which involves bone and tissue ingrowth into the matrix, including the establishment and maintenance of a vascular bed in the matrix, eventually resulting in new bone formation (mineralization). Unlike many existing scaffolds, the patient's vascular supply is able to readily penetrate through the porous body of the implant, which supports the development of new blood vessels that are essential to bone repair and allows the formation of a robust vascular bed. Advantageously, the inventive implant supports vascularization throughout the entirety of the matrix, resulting in not just in-growth of bone tissue at the exterior surface of the implant (1-2 mm), but "through-growth" of bone tissue through the entire matrix body. For example, in long bones, a proximal to distal bone growth from adjacent bone, which remains aligned with the original implant position can be observed. As bone tissue infiltrates the matrix and mineralizes, the porous body is slowly degraded and absorbed by the patient's body. More preferably, at about 6 weeks after implantation, the implant is preferably at least about 75% resorbed, more preferably at least about 85% resorbed, and even more preferably at least about 95% resorbed. In other words, at about 6 weeks after implantation, the treated area will comprise less than about 25% carbonaceous material from the implant, more preferably less than about 15% carbonaceous material, and even more preferably less than about 5% carbonaceous material, based upon the total initial carbon content of the implant taken as 100%. The terms "resorpotion" and "bioresorption" are used interchangeably herein and mean that the material is broken down by the body over time and does not require mechanical removal from the body. A particularly unexpected aspect of the invention is that direct displacement/replacement of the scaffold by the new tissue will preferably be observed, as opposed to overgrowth of tissue. This through-growth of bone in alignment with the original implant position is a surprising and particularly advantageous aspect of the present invention.

It will be appreciated that the inventive implant will have additional uses beyond traditional bone void filling, including arthroplasty, fracture repair, and reconstructive surgery. The implant could also have applications in plastic and cosmetic surgery where bone modifications are required. As noted above, the implant can also serve as a drug delivery device for orthopaedic applications, providing local delivery of therapeutic agents, osteogenic factors (such as BMPs and other biological response modifiers), and factors to inhibit bone resorption (such as bisphosphonates).

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

The invention described herein is discussed primarily with respect human-based therapies; however, it will be appreciated that the treatment can be applied for clinical research or therapeutic treatment to any suitable animal, including, without limitation, dogs, cats, and other pets, as well as, rodents, primates, horses, cattle, etc. Additional advantages of the invention will be apparent to those in the art upon review of the disclosure herein and the working examples below.

EXAMPLES

The following examples set forth methods in accordance with the invention. It is to be understood, however, that these examples are provided by way of illustration and nothing therein should be taken as a limitation upon the overall scope of the invention.

Example 1

Initial Biomaterial Analysis for Mechanical Properties

Extensive studies into the development of biomaterials with a particular focus upon bone and nerve grafting using tissue engineered scaffolds were previously carried out on poly-epsilon-caprolactone-hydroxyapatite (PCL-HA) composites and chitosan-collagen composites. A number of model systems for the evaluation of bone biocompatibility were also developed previously. A novel PCL-HA composite was developed to promote vascularization of the bone graft substitute, as PCL has been approved by the FDA for use in medical and drug delivery devices, and studies have demonstrated its biocompatibility. However, its structural properties proved to be less than ideal for use as a bone void filler, and its degradation and resorption rates were too rapid to provide structural support during bone ingrowth. Thus, a series of preliminary studies were carried out on carbon foam scaffolds for bone grafting and regeneration.

Figure 2:
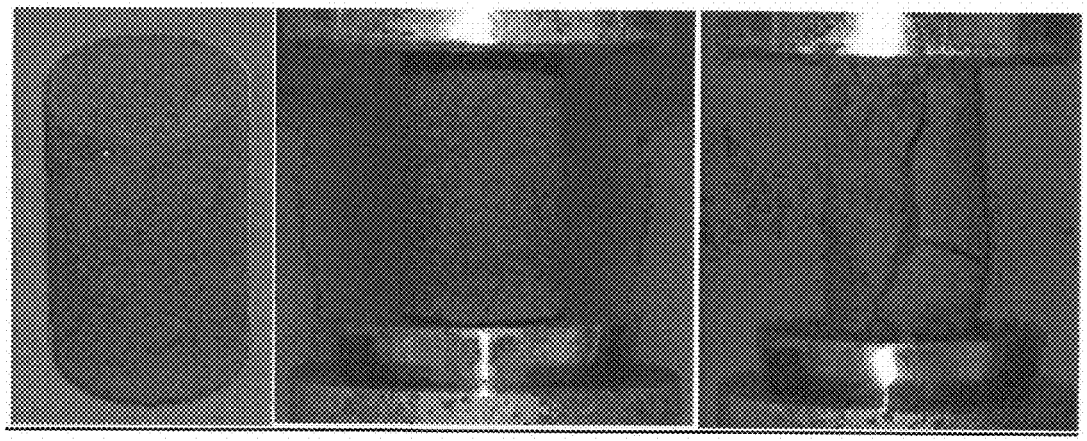
FIG. 2 is a photograph of carbon foam cylinders from the mechanical testing in Example 1.

Mechanical testing of a carbon foam material DUOCEL® with a pore size of about 120 µm was performed with strict adherence to the ASTM Standard Test Method for Compressive Properties of Rigid Plastics (ASTM D-695-02a). The material was machined into cylindrical-shaped specimens with a diameter of 1 cm and thickness of 2 cm. The specimens were then tested for mechanical properties using an MTS 858 Bionix material testing system (MTS Model 858, Eden Prairie, Minn.). Load and deflection data were measured and collected by the MTS system every 0.1 seconds. Each specimen was tested in compression loading from 0N to complete structural failure at a loading rate of 1.3 mm/min. The maximum stress was then determined, and the results are shown in FIG. 2, and the table below.

TABLE 1

Mechanical Properties of Carbon Foam

|  | Ultimate Load (N) | Ultimate Stress (MPa) | Ultimate Displacement (mm) | Ultimate Strain (MPa) |
| --- | --- | --- | --- | --- |
| Average | 1693 | 12.57 | 0.94 | 0.026 |
| SD | 240 | 1.75 | 0.41 | 0.006 |
| Max | 2013 | 14.91 | 1.99 | 0.040 |
| Min | 1192 | 8.91 | 0.67 | 0.020 |

The significant parameter is "ultimate stress" which yielded a value of 12.57 MPa, a value equivalent to the ultimate stress capability of low-medium density trabecular bone. The data indicate that the carbon foam meets or exceeds the properties of human trabecular bone tested under similar conditions (10-50 MPa), indicating that carbon foam can achieve appropriate mechanical properties to serve as a bone void filler, even for weight-bearing applications.

Example 2

In Vitro Biocompatibility of Carbon Foam

1. Initial Testing

Figure 3:
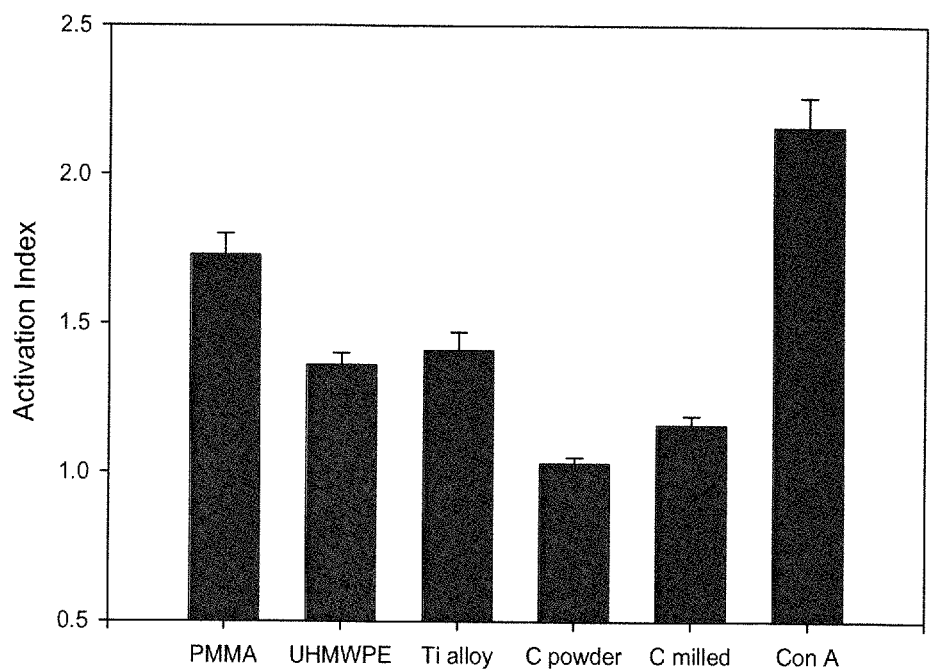
FIG. 3 is a graph of the activation indices for each of materials tested in Example 2.

Initial biocompatibility of carbon foam was conducted using a cell culture system developed in our laboratory for the evaluation of patient hypersensitivity to orthopaedic biomaterials. Carbon in both powdered and milled fiber forms was evaluated using mononuclear cells (MNCs) obtained from 40 osteoarthritic patients under investigation for biomaterial sensitivity, along with other conventional biomaterials (polymethylmethacrylate (PMMA), Ti alloy, ultra-high-molecular-weight polyethylene (UHMWPE)). Peripheral blood was obtained from patients and MNCs were separated using Histopaque gradients. Cell suspensions of $2.5 \times 10^6$ cells were dispensed into wells containing various concentrations of biomaterial particles. Wells with no particles (negative control) or with Concanavalin A (ConA) (positive control) were also included on the plate. Plates were incubated for 6 days. Next, 20 µl of MTT solution (5 mg/ml) were then to each well, and incubation continued at 37° C. for 6 hours. The medium was then replaced by 10% sodium dodecyl sulphate (SDS), and the optical density (OD) of the resulting solution was read at 590 nm. Cell responses were then determined. Stimulation indexes (SI) for each response were calculated by comparison with background proliferation (medium control). The data (FIG. 3) indicate that carbon in either powder or milled fiber form provoked extremely low levels of cell activation when compared with other orthopaedic biomaterials, and generated a significantly ($p<0.01$) lower response than PMMA, which is commonly used as a bone void filler during current orthopaedic procedures. The data suggest that carbon implantation materials or degradation products do not pose an overt risk of either inflammatory reactions or tissue toxicity if used as bone void fillers.

2. Additional In Vitro Testing

Figure 4:
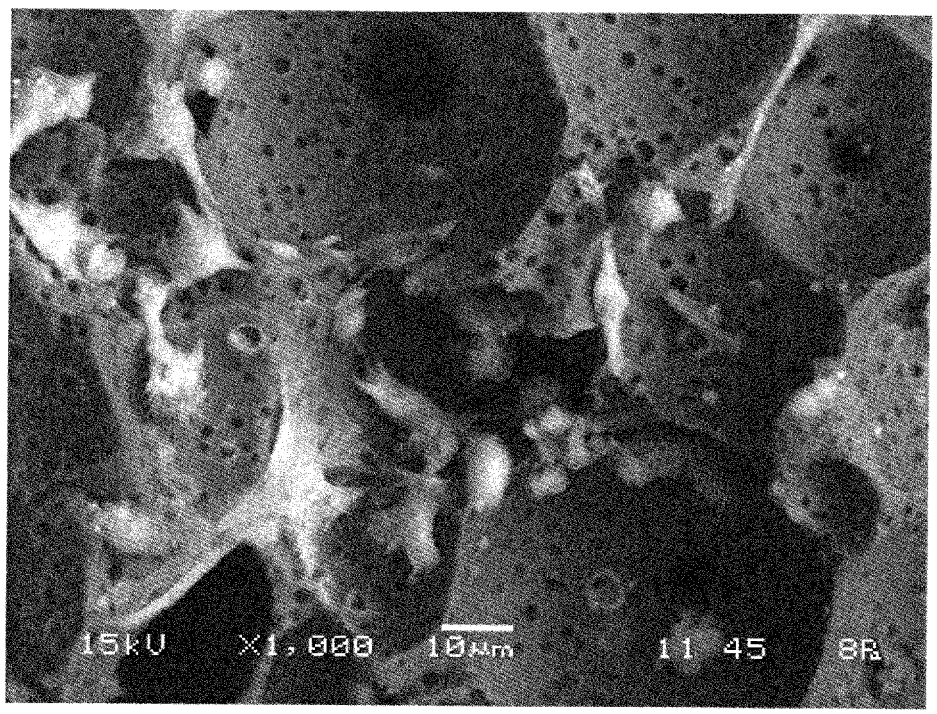
FIG. 4 is an SEM image of cellular attachment and colonization on a carbon foam scaffold from Example 2.

Further in vitro testing was conducted to evaluate cellular growth characteristics on carbon foam substrates using the RAW 264.7 mouse mono cyte/macrophage cell line, and cells from rat bone marrow cultures induced to differentiate into osteoblasts in DMEM media supplemented with glycerol phosphate, L-ascorbic acid, and dexamethasone. Aliquots of 50 µl suspensions ($3.5 \times 10^6$ cells/nil) were loaded onto carbon foam scaffolds in 6-well plates and left undisturbed in a 37° C. incubator for 3 hours to allow cells to attach to the scaffold. At day 3, samples were harvested for morphological evaluation. Scaffolds with cultured cells were fixed with 1.5% glutaraldehyde (Fisher Scientific, US) for 30 min. at 4° C., and the samples were washed twice in PBS and then exposed to 2% osmium tetroxide (Sigma-Aldrich, US) for 30 min. The samples were then rinsed in distilled water, and dehydrated through a graded series of ethanol (50, 70, 90, and 100%) for 2-5 min., with and the dehydration completed in hexamethyl disilazane (HMDS) (Fluka, Germany) for 10 min. After air-drying, the samples were mounted onto SEM stubs and images were observed at 10 kV. Images were evaluated for cellular attachment and surface occupancy on the scaffolds. The results are shown in FIG. 4 and indicate that the RAW 264.7 cells had adhesion and colonization on the scaffold after three days in culture. Dye exclusion techniques also revealed a high level of viability.

3. Surface Modification of Carbon Foam

Figure 5:
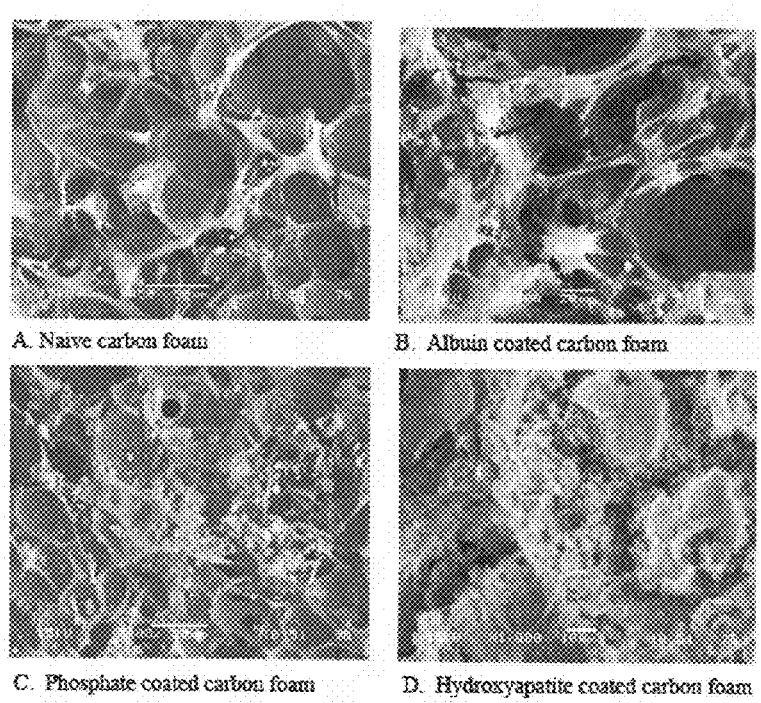
FIG. 5 are SEM images of carbon foam scaffolds with various surface treatments/coatings from Example 2.

Surface modification of the carbon foam scaffold was investigated in a number of cell culture studies using bone marrow derived osteoblasts. Scaffolds were coated with serum albumin, phosphate, and hydroxyapatite. The data (FIG. 5) indicated that cultures of bone marrow-derived osteoblasts on carbon foam scaffolds for 7 days resulted in cells that developed a spindle or polygonal morphology. The cytoplasmatic projections evidently attached to the scaffold so as to facilitate cell adhesion and spread. Extracellular matrix (collagen-like fibers) produced by osteoblasts was clearly present at intercellular regions indicating cell colonization. Optimal cell growth and scaffold pore penetration was obtained on carbon foam scaffolds coated with albumin, suggesting that protein modification improved cell adhesion and colonization. However, cell growth also appeared adequate on uncoated carbon foam and moderate on scaffolds modified by phosphate. Coating with hydroxyapatite at the level applied in this experiment resulted in occlusion of pores within the carbon foam structure, which significantly reduced cell adhesion and surface colonization. Further testing and scaffold pore size modification will be required to optimize carbon foams coated with hydroxyapatite. Evaluation of cell viability using dye exclusion techniques revealed a high level of viability within the cultures, suggesting that hydroxyapatite coating preparations reduced cell attachment rather than exerted a toxic effect upon the cells.

Example 3

In Vivo Biocompatibility of Carbon Foam

Initial in vivo testing of carbon foam scaffolds was carried out to further evaluate the material for biocompatibility and determine if cellular ingrowth within the porous structure could be readily achieved. Two forms of carbon (DUOCEL®) with widely disparate structural properties were selected for testing: (1) A closed cell carbon foam (pore size ~120 µm); and (2) An open cell carbon foam (pore size ~1 mm). Initial testing was conducted using a previously-developed murine air pouch implantation model (Wooley et al. *Inflammatory*

*responses to orthopaedic biomaterials in the murine air pouch.* Biomaterials 2002; 23:517-526; and Ottaviani et al. *Inflammatory and immunological responses to hyaluronan preparations. Study of a murine biocompatibility model.* J Bone Joint Surg Am 2007; 89(1):148-157).

Balb/c mice weighing 20-25 g were divided into two implantation groups, and air pouches were established 6 days before carbon foam implantation. An area of the dorsal-lateral skin (2 cm²) was cleaned with alcohol and shaved to provide the pouch site. A subcutaneous injection of 2.5 ml of air was carried out at a single site with a 25-gauge needle and 20 ml syringe. The air pouches were re-injected with 1 ml of air on alternate days for 6 days to establish a fluid-filled pouch beneath the skin Carbon foam scaffolds (5 mm diameter, 2 mm thick discs) were surgically implanted into the air-pouch through a 1 cm incision, and the mice were observed for any adverse effects of the biomaterial. Animals were sacrificed fourteen days after implantation, and both pouch tissue and the carbon foam scaffolds were recovered for histopathological evaluation.

Figure 6:
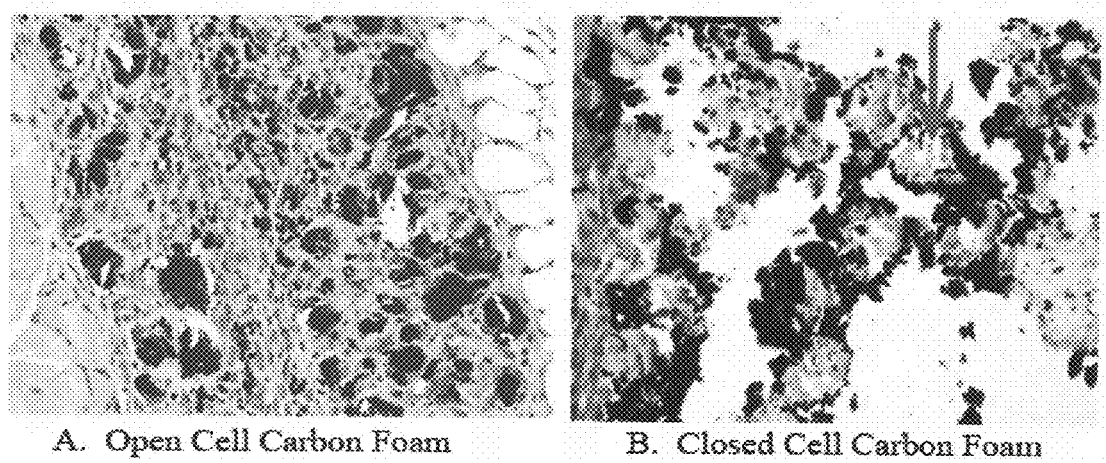
FIG. 6 are photos of hematoxylin & eosin stained sections of recovered implants from Example 3.
Figure 7:
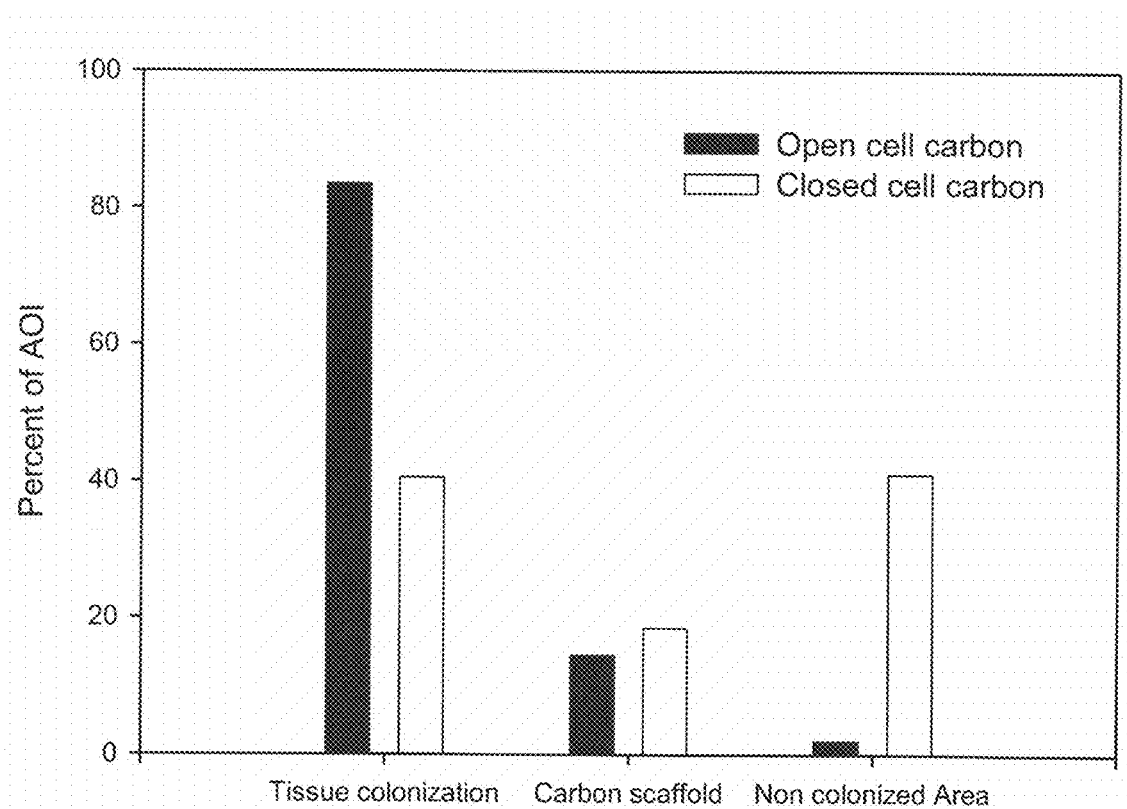
FIG. 7 is a graph comparing the colonization between the open-cell and closed-cell foams from Example 3.

Gross examination of the air pouch indicated a mild to moderate degree of inflammation in response to both forms of carbon foam. Histological examination of the recovered implant sections stained with hematoxylin & eosin (H&E) (FIG. 6) indicated complete fibrous tissue colonization within the open cell carbon foam, and substantial colonization within the closed cell material. Image analysis (FIG. 7) to determine tissue occupancy within the carbon foam scaffold reflected the microscopic appearance, and indicated that 98% of the open cell scaffold was occupied by carbon foam or fibrous tissue, compared with only 49% of the closed cell scaffold. The data indicate that the level of porosity and scaffold pore size exert a strong influence on the level of fibrous tissue ingrowth. However, it appears that neither fibrous tissue ingrowth nor blood vessel formation (see arrow, FIG. 6B) are excluded by a scaffold pore size of approximately 120 µm.

Example 4

Carbon Foam Bone Scaffolds in Animal Models of Traumatic Injury

Experiments were conducted to demonstrate the performance of carbon foam scaffolds as bone void fillers in animal models of traumatic injury, including both a weight-bearing model (the rat femur critical defect) and a non weight-bearing model (the rat calvarial defect). The rat femur critical defect involved a 10-mm bone segment resected from the femoral shaft, while the rat calvarial defect involved a 5-mm diameter bone segment resected from the parietal bone. In each case, the resected bone was replaced with a carbon foam scaffold of similar size and shape. Lewis rats weighing approximately 220 g were used in this study. Animals were quarantined for one week prior to implantation surgery. For each experiment, the rats were subcutaneously injected with 0.05 mg/kg of buprenorphin and 5 mg/kg carprofen one hour before surgery for preventative analgesia. The rats were then anesthetized by i.p. injection of a mixture of xylazine (8 mg/kg) and ketamine (70 mg/kg). Sterile ophthalmic ointment was applied to the eyes to prevent drying of corneas during surgery.

Figure 8:
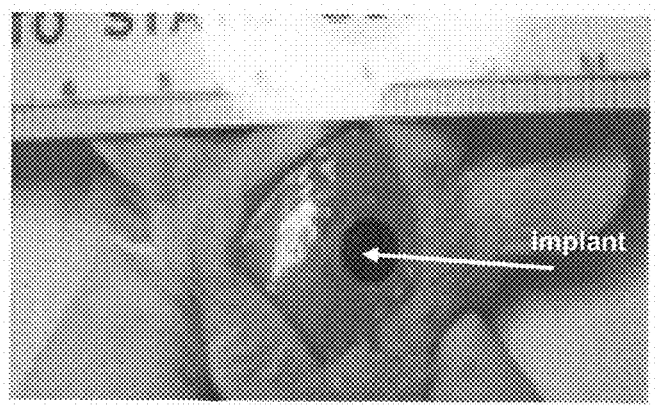
FIG. 8 is a photograph of the implant for the calvarial defect model from Example 4.

For the calvarial defect, a 2-cm² section of the head was shaved using electric animal clippers and sterilized by scrubbing with povidone followed by a rinse of 70% alcohol. A portion of the scalp was removed, and then a circular section of the parietal bone was resected. A carbon foam disc DUOCEL® of a similar shape and size (6 mm diameter, 2 mm thick) as the resected bone piece was then seated into the parietal cavity (FIG. 8), the skin flap was replaced and sutured. The wound was cleaned and rinsed with PBS containing antibiotics to prevent the local infection.

Figure 9:
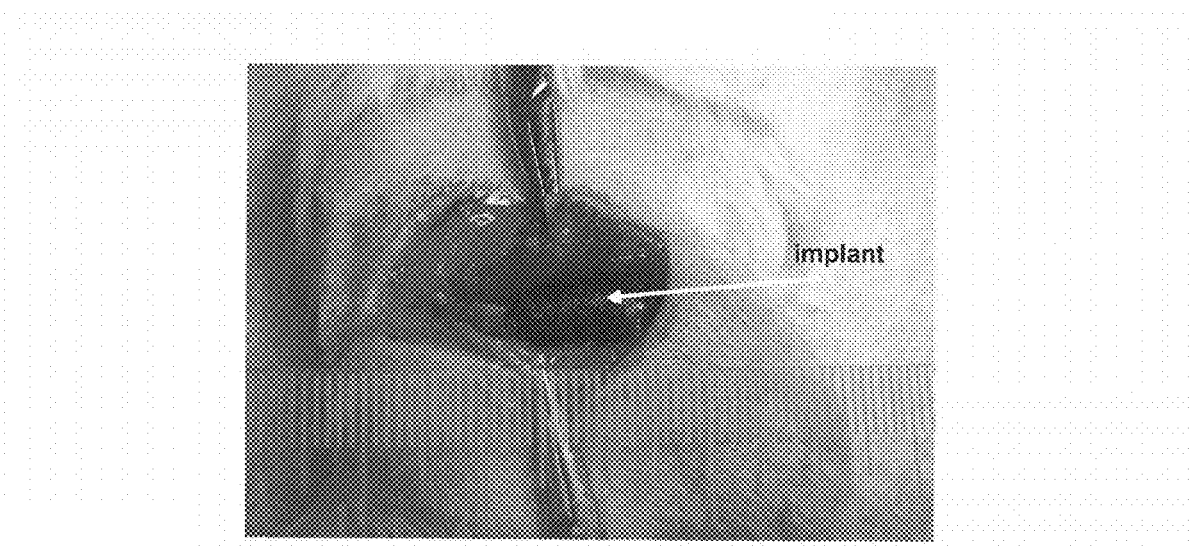
FIG. 9 is a photograph of the implant for the femoral defect model from Example 4.

For the weight-bearing experiment the left hind limb of each animal was shaved using an electric animal clipper and sterilized by scrubbing with povidone followed by a rinse of 70% alcohol. An incision was then made along the femur and a mid-shaft bone segment resected. A cylindrical carbon foam (DUOCEL®) bone graft with a similar shape and size (4 mm diameter, 6-8 mm thick) as the removed bone segment was seated into medullary canal of the distal part of the femur shaft and the opposite metaphysic, and fixed with an intramedullary pin. (FIG. 9) The wound was cleaned and rinsed with PBS containing antibiotics to prevent local infection. The muscular layer around the femur was then closed with absorbable sutures and the skin sutured with nylon suture. A Micro CT was used to confirm the success of graft implantation in the femur for the weight-bearing group. Animals were initially placed into the holder of a Scanco Viva CT 40 CT scanner, with the femur oriented perpendicular to the x-ray beam. A scout view was performed to verify the position of the limb. The scan was performed using an energy level of 70 kV, a current of 114 µA, and an integration time of 200 ms. The scan was performed at medium resolution, with a beam thickness of 25 µm.

Post-operation all animals were given 1.0 ml of sterile warm saline subcutaneously and placed in a clean cage warmed by a heat lamp for at least 4 hours, with close observation until the rats recovered from anesthesia and were returned to normal housing. The rats were monitored in an animal facility with a normal diet for 6 weeks before being sacrificed under $CO_2$. Animals from the weight-bearing group were also evaluated for return to normal gait over time. Full ambulatory weight bearing was observed in rats with repaired femoral defects around one week post-operation.

Figure 10:
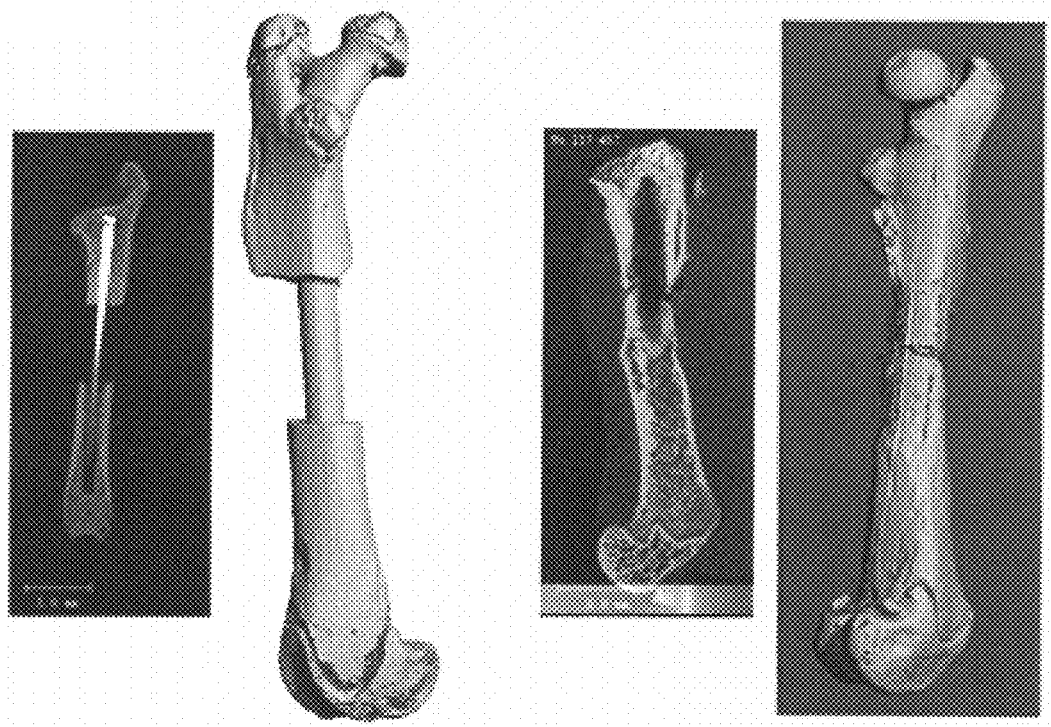
FIG. 10 shows the CT scans and 3-D modeling of the implant from Example 4.

For the weight bearing-group, a Micro CT scan was repeated 6 weeks after the initial scan before retrieving the graft. Data was analyzed using the manufacturer's supplied analysis software to calculate the bone volume of the fracture site and create a three-dimensional image. The region of interest was defined by contouring the slices to include the femoral defect. The evaluation program used a threshold of 62-690 of 1000 intensity, to include less dense bone around the defect site. A Gaussian filter of sigma 1.2 and support 2 was applied to reduce noise in the image. The same settings were used to create the image of the entire femur, except that the contours encompassed the entire femur for that evaluation. The grafts were then retrieved, and subjected to further investigation using CT analysis, biomechanical tests of bone strength, and histology of the recovered graft and bone. The results for the rat femoral defect are shown in FIG. 10. The internal fixation pin was removed prior to imaging at six weeks to permit accurate assessment of the biomechanical strength of the interfaces and histological sectioning. The six week post operative image clearly illustrates the capacity of the carbon foam to provide a scaffold for bone void repair. The result indicates significant repair of the femoral critical defect, with reconstruction of the bone cortices in a consistent and accurate manner. The carbon foam was essentially displaced (resorbed) during the bone void repair, suggesting the capacity of the scaffold to remodel as bone repair progresses.

Figure 11:
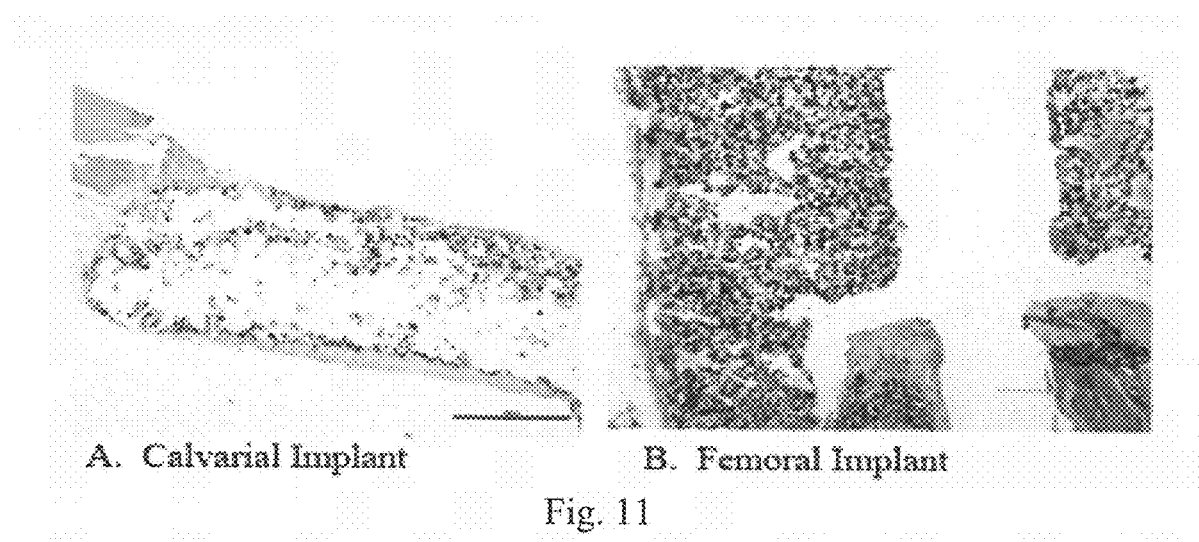
FIG. 11 are images of histology slides for scaffold and the surrounding bone harvested from the animals in Example 4.
Figure 12:
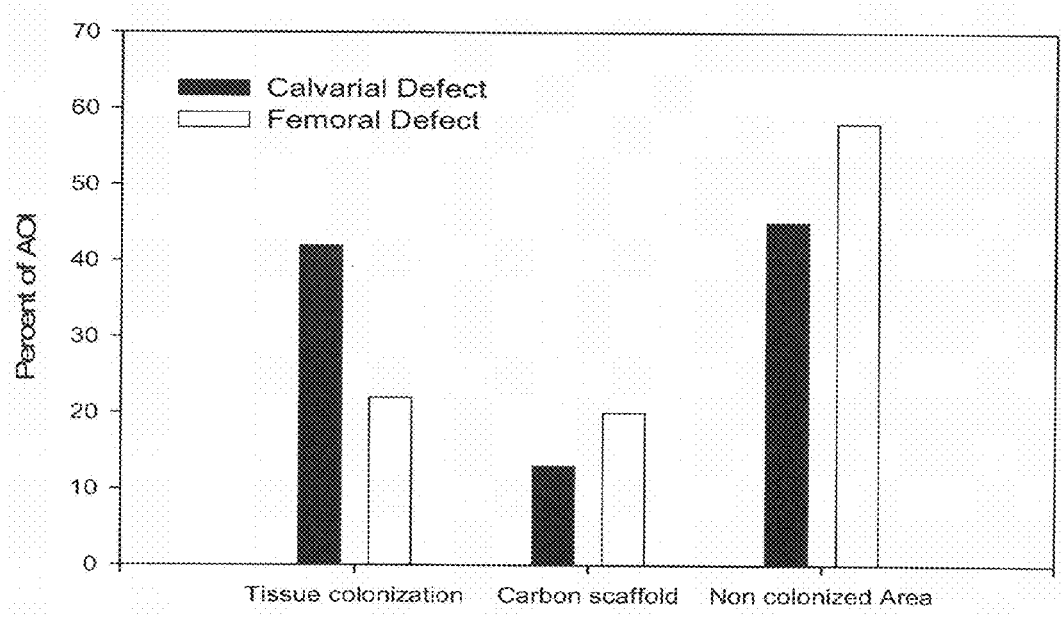
FIG. 12 is a graph of tissue colonization of the two defect models in Example 4.
Figure 13:
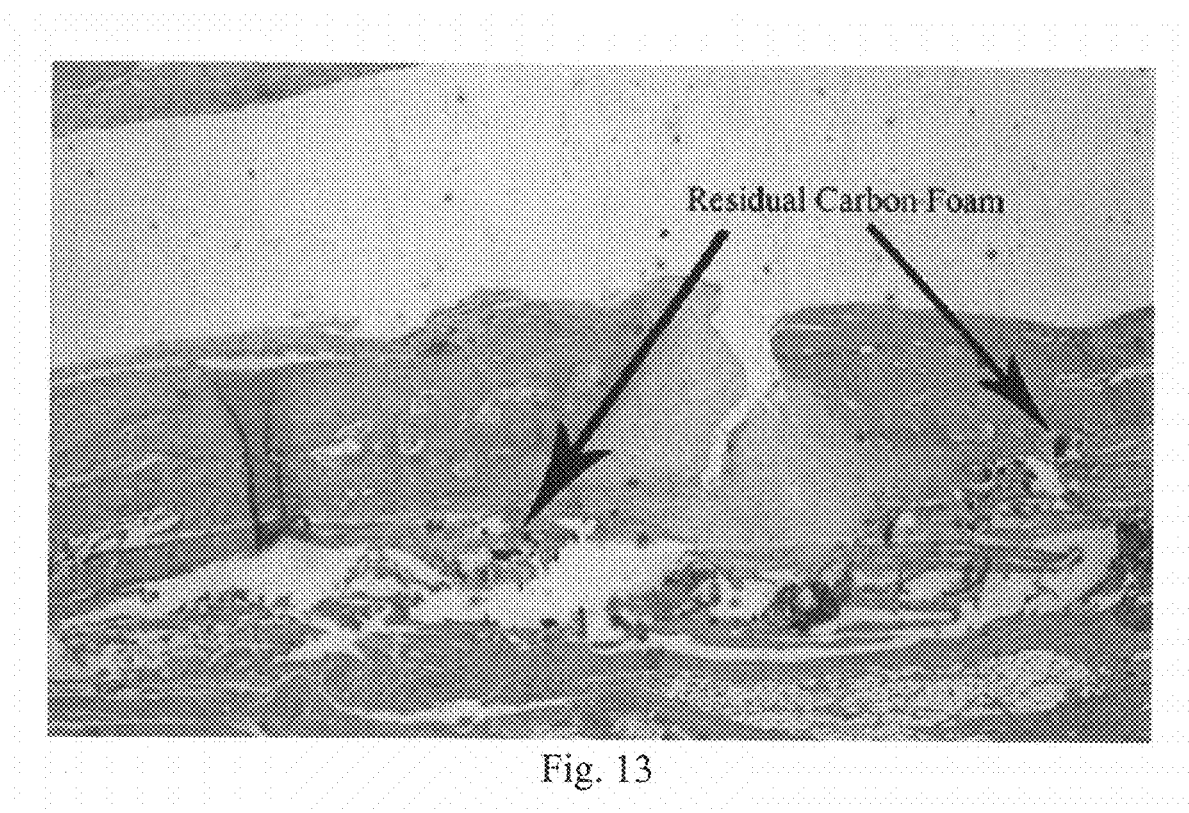
FIG. 13 is an image of harvested scaffold and tissue from the femoral defect model in Example 4.

After sacrificing, broad sections of the scaffold and the surrounding bone were harvested for histological evaluation. Samples were decalcified using EDTA solution, and sections were stained with H&E and Masson's Trichrome. Histology slides (FIG. 11) revealed intact tissue integration at the scaffold/bone interface in both the calvarial and the femoral defect models. Tissue penetration was observed to a depth of approximately 1 mm in both models. However, tissue mineralization with the appearance of lamellar bone was more prominent in the calvarial defect than the femoral defect, where predominantly fibrous tissue was observed. The slides from the weight-bearing group confirmed the interpretation of the CT images, and revealed new bone formation contiguous with proximal and distal portion of the resected femur. The sections also revealed the remarkable degradation and resorption of the carbon foam scaffold within the periosteal tissues, with proximal to distal regrowth of bone through the carbon foam scaffold, instead of overgrowth and fusion typically seen with implants. Image analysis (FIG. 12) to determine tissue occupancy within the carbon foam scaffold at the bone/implant interface revealed a higher level of tissue colonization (42% tissue, 13% carbon scaffold) in the calvarial implant compared with the femoral implant (22% tissue, 20% carbon scaffold) after 6 weeks of implantation. The mechanical strength of the scaffold/bone interface was not determined in this preliminary study, and the reasons for the variations observed between the load bearing and non load bearing defect models remain to be determined. In additional experiments, no residual scaffold could be detected within the repaired bone for the femoral defect model, and the image analysis of tissue exterior to the cortices indicated a carbon foam content of 4%, compared with a 26% carbon content (FIG. 13) in sections from voids harvested immediately postoperatively.

Example 5

Evaluation of Osteoblast Integration into Porous Carbon Foam Matrix

Figure 14:
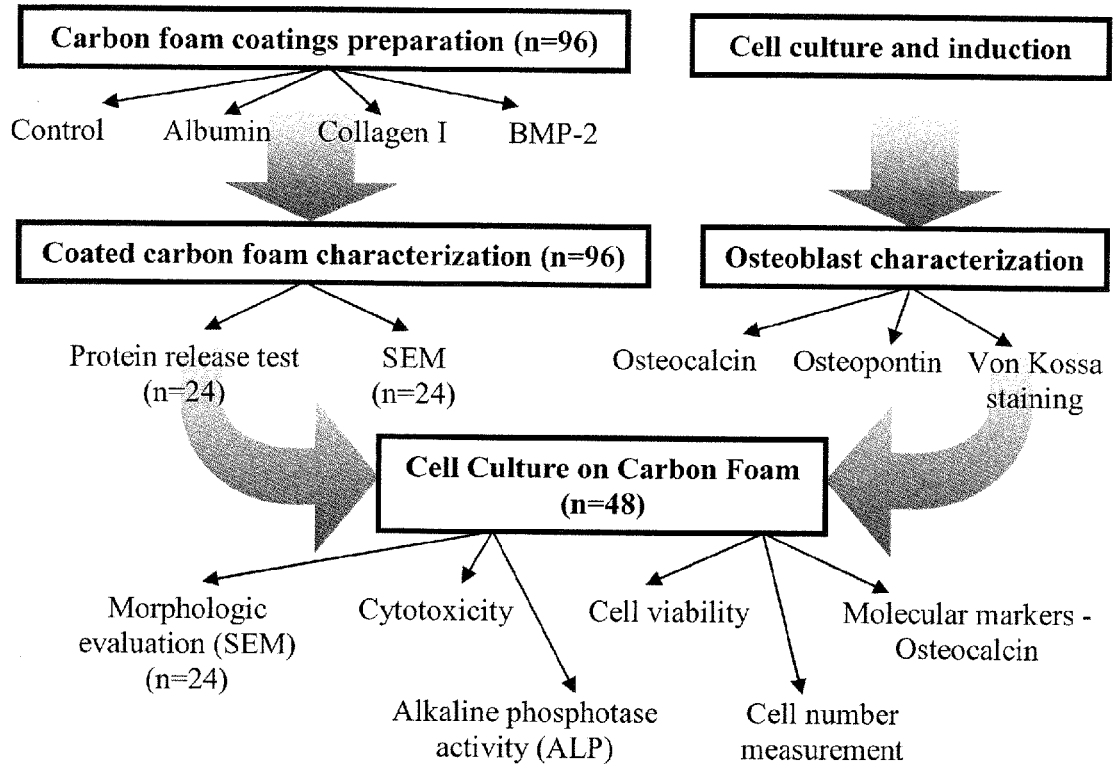
FIG. 14 is a flowchart of the protocol followed in Example 5.

The objective of this study was to examine several factors associated with cell attachment to the surface (osteoblast integration) of the carbon foam scaffold and study the effects of various coatings applied to the carbon foam scaffold. A flowchart of the study protocol is shown in FIG. 14.

1. Materials and Methods

Figure 15:
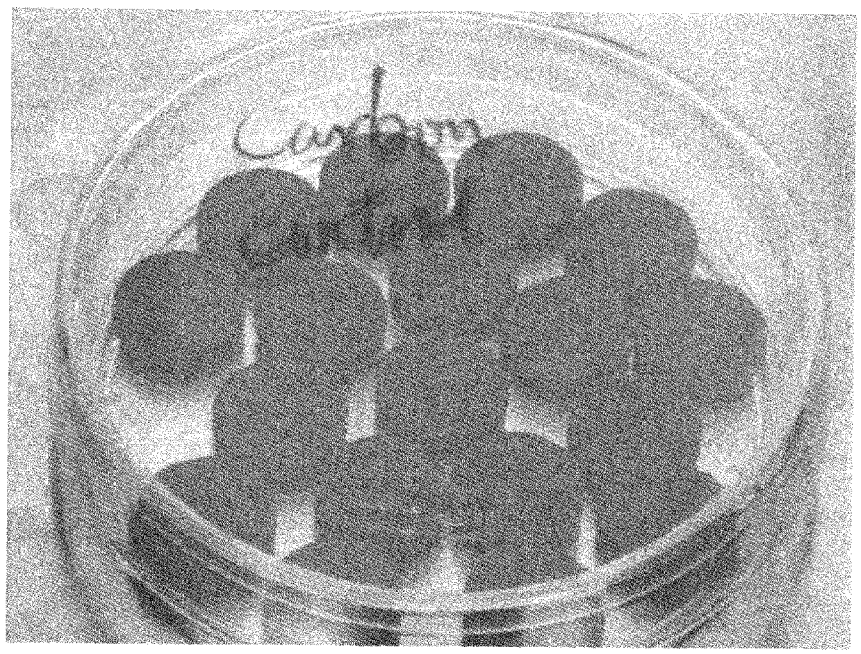
FIG. 15 is a photograph of control carbon discs used in Example 5.

Reticulated vitreous carbon foam (DUOCEL® RVC carbon foam; ERG Materials and Aerospace Corporation, Oakland, Calif.) with 80 PPI, 3% relative density and pore sizes ranging from 40-250 µm was used for these experiments. Four different types of carbon foam conditions were examined: (A) Original (uncoated) carbon foam; (B) Albumin-coated carbon foam; (C) Collagen type I-coated carbon foam; and (D) Bone Morphogenetic Protein 2 ("BMP-2") coated carbon foam. The original (uncoated) carbon foam sample group was selected as the baseline for comparison of the other sample groups. A total of ninety six discs (24 for each sample group) were machined and cut into 1-cm diameter and 2-mm thick cylinders as shown in FIG. 15. The discs were cleaned with alcohol to remove residual carbon dust from machining.

2. Carbon Foam Coatings Preparation

The discs were subjected to one of 3 pretreatments: (1) immersion in 10 µg/ml human serum albumin (HSA) with distilled water for 24 hours at 37° C.; (2) immersion in collagen type I solution for 24 hours at 37° C.; or (3) immersion in 10 µg/ml BMP-2 with distilled water for 24 hours at 37° C. Carbon foam discs immersed in distilled water served as a control. A low pressure vacuum system was used to facilitate the absorption of the coatings into the pores inside the carbon foam discs. The treated carbon foams were then carefully centrifuged to remove excessive solution. All samples were then air-dried in a biology hood overnight. Residual pretreatment solutions were collected and measured for albumin, collagen I, or BMP-2 concentration using an enzyme-linked immunosorbent assay (ELISA).

3. Coated Carbon Foam Characterization a. In Vitro Protein Release Test:

Coated carbon foam discs (6 samples/group) were placed in a 24-well plate with 1 ml of phosphate buffer solution (PBS) with pH 7.4 release buffer. The carbon foam discs were then incubated at 37° C., the release buffer was collected and replaced with fresh buffer daily for 6 days. All samples were then stored at −20° C. until analysis. The albumin, collagen type I or BMP-2 released from the samples was then assayed using ELISA. Duplicate series of 8 two-fold dilutions of each coated material ranging from 1,000 to 4 ng/ml were prepared, and this served as a standard data set to determine protein concentrations of the sample groups. The absorbance of the samples and standards were measured at 450 nm wavelength using a microtiter plate reader, and the cumulative release of albumin, collagen type I or BMP-2 was extrapolated from the standard curves.

b. Scanning Electron Microscopy (SEM)

All the samples were mounted onto SEM stubs, and the porous properties of the carbon foam (SEM images) were observed and evaluated at 10 kV or 15 kV using a scanning electron microscope.

4. Cell Culture and Induction

Bone marrow cells (BMC) were obtained from the bone marrow of female Lewis rats. Following euthanasia by $CO_2$ asphyxiation, femora were aseptically excised, the metaphyseal ends were cut off and the marrow was flushed from the medullary cavity with 10 ml of Dulbecco's Modified Eagle medium (DMEM) using a syringe with a 22-gauge needle. Cell clumps were dispersed by repeatedly pipetting the cell suspension, and low-density bone marrow mononuclear cells isolated using density centrifugation over Histopaque®-1083. Cells were then washed with PBS, and prepared for culture and differentiation of osteoblasts. BMCs were induced to differentiate into osteoblasts in complete media consisting of DMEM supplemented with 10% fetal bovine serum (FBS), 10 mM β-glycerol phosphate, 100 µM L-ascorbic acid, and 10 nM dexamethasone, 2 mM glutamine, 100 U/ml penicillin, 100 ug/ml streptomycin, and $10^{-4}$ M L-ascorbic acid. The induced BMCs were then seeded on the coated carbon foam discs and cultured in an incubator at 37° C. for seven days.

5. Osteoblast Characterization a. Osteocalcin, Osteopontin, and Collagen Type I

On the second passage, the induced osteoblasts were fixed in 4% paraformaldehyde, permeated with 0.01% Triton X-100 in PBS, and incubated in 1% block serum for 1 hour at 37° C. The cells were then incubated with anti-osteocalcin, osteopontin, or collagen type I for 1 hour, and visualized using Alexa Fluor conjugated (Molecular Probes, Eugene, Oreg.) (for osteocalcin and osteopontin) or Alexa Fluor 488-conjugated (Molecular Probes, Eugene, Oreg.) (for collagen type I) secondary antibody. The cells were examined under a fluorescence microscope. Nuclei were counterstained with DAPI (Molecular Probes, Eugene, Oreg.).

b. Von Kossa Staining

The presence of calcium deposits was demonstrated by von Kossa staining. Potential osteoblasts were rinsed in PBS and fixed in 4% paraformaldehyde for 30 minutes, and then incubated with 1% silver nitrate solution (Sigma-Aldrich, US) under ultraviolet light for 20 minutes. Un-reacted silver was removed by 5% sodium thiosulfate (Sigma-Aldrich, US) for 5 minutes. The stained slides were then observed under microscope after permanent mounting.

6. Cell Culture on Carbon Foam

Induced osteoblasts in 50 μl suspensions (3.5×10⁶ cells/ml) were respectively loaded onto each scaffold in 24-well plates. The scaffolds were left undisturbed in a 37° C. incubator for 2 hours to allow cells to attach to the scaffold, after which the seeded cells on materials were kept in culture using the same osteogenic media. Medium was changed every 3 days, and at Day 7 samples were harvested for morphological and biochemical evaluation. Culture dish cells were used as the control.

7. Morphological Evaluation

To prepare for SEM examination, membranes with Day 7 culture cells were fixed with 2% glutaraldehyde for 60 minutes at 4° C. The samples were then washed twice in PBS and exposed to 2% osmium tetroxide for 60 minutes. Once the samples had been rinsed in distilled water, they were dehydrated through a graded series of ethanol (20%, 40%, 60%, 80%, 95%, and 100%) for 5 minutes. The dehydration process was completed in hexamethyl disilazane (HMDS) for 10 minutes. After air-drying, the samples were spot-coated with gold and mounted onto SEM stubs. SEM images were observed at 10 kV or 15 kV, and saved for the morphology evaluation of the induced osteogenic cells on the scaffolds.

8. Cytotoxicity

Cytotoxicity of carbon foams was quantitatively assessed by the measurement of lactate dehydrogenase (LDH) leakage. A CytoTox 96® assay was used to measure the ratio of lifeless cell to live cells on the bone or composite scaffold. LDH is an outstanding indicator of cell death and damage. Lifeless cells release LDH during culturing, therefore, it is essential to collect the cultured medium along with the lysis buffer supernatant. 10 μl of aliquots of the medium was mixed with 200 μl LDH reagent, and the cultured medium and lysis buffer solutions for each of the four groups were transferred to their corresponding well. A spectrophotometer (Spectra MAX Gemini XS) was used to measure the absorbance of solutions at 490 nm wavelength. Higher readings correspond to a higher toxic environment for osteogenic cells.

9. Cell Viability

Cell viability was assayed by analyzing the mitochondrial activities in the cultured cells on the discs. The alamarBlue® assay (BioSource, US) was used to determine the activity of the cells after 7 days of cell culture. AaamarBlue® reagent is a valuable tool used to ensure cell proliferation on the discs through correlating cell number to the absorbance values. In contrast to cytotoxicity tests, the cultured medium was removed completely with PBS and fresh medium was added to cover the composite samples. 3 ml of new conditioned media supplemented with 200 μl of alamarBlue® was added to each well, and incubation was continued at 37° C. with 5% $CO_2$ for 4 hours. The culture medium was then transferred to a 96-well plate and read on a spectrophotometer (Spectra MAX Gemini XS) at excitation wavelength 570 nm, emission wavelength 600 nm, and data was collected and analyzed using SoftMax PRO. The alamarBlue® absorbance of DNA values were calculated for each sample.

10. Cell Number Measurement

Cell numbers were determined by a fluorometric quantification of DNA on the carbon foam construct. After the alamarBlue® assay, the cell-scaffolds were rinsed with PBS, followed by 1 ml lysis buffer and 2 minutes ultrasonic. The lysate was then saved into a specific tube. 100 μl of supernatant sample were mixed in 1.5 ml of 200 ng/ml Hoechst 33258 fluorescent dye (Sigma-Aldrich, US) and read at EX 350 nm and EM 455 nm by fluorometer. The DNA concentration in the samples was determined against a DNA standard curve.

11. Alkaline Phosphatase (ALP) Activity

ALP activity by osteogenic cells was measured using a spectrophotometer. After the previous freeze-thaw cycle (freeze at −80° C. for 30 minutes, and thaw at 37° C. for 30 minutes) and homogenization for the DNA assay, 100 μl of the sample was removed from the lysate to which 100 μl of p-nitrophenyl phosphate solution was added. After 30 minutes incubation at 37° C., the production of p-nitrophenol in the presence of ALP was measured at an absorbance of 405 nm wavelength. The measurement of the ALP assay was normalized against the amount of total DNA in each sample.

12. Molecular Markers (Osteocalcin)

Cell lysates were used for the assay of osteocalcin using a sandwich ELISA. 2 μg/ml of primary antibody was coated and incubated overnight at 4° C. The plates were washed 3 times with PBS, dispensed with 200 μl of 5% milk and incubated at 37° C. for 4-6 hours. Samples with 50 μl of supernatant were added to the coating plate and incubated overnight at 4° C., followed by washing the plate and adding 100 μl of 1 μg/ml antibody, followed by incubating at 37° C. for 1 hour. Plates were washed and then 20 μl of streptavidin was added into 10 ml of PBS, and incubated at 40° C. Next, 2 pNPP was dissolved per 10 ml of diethanolamine buffer, followed by incubation at 37° C. in the dark for 5-20 minutes. A spectrophotometer (Spectra MAX Gemini XS) was used to measure the absorbance of solutions at 405 nm wavelength, and the absorbance of ELISA was normalized against the amount of total DNA in each sample.

13. Results a. Characterization of Coated Carbon Foam (1) Protein Release Test

Figure 16:
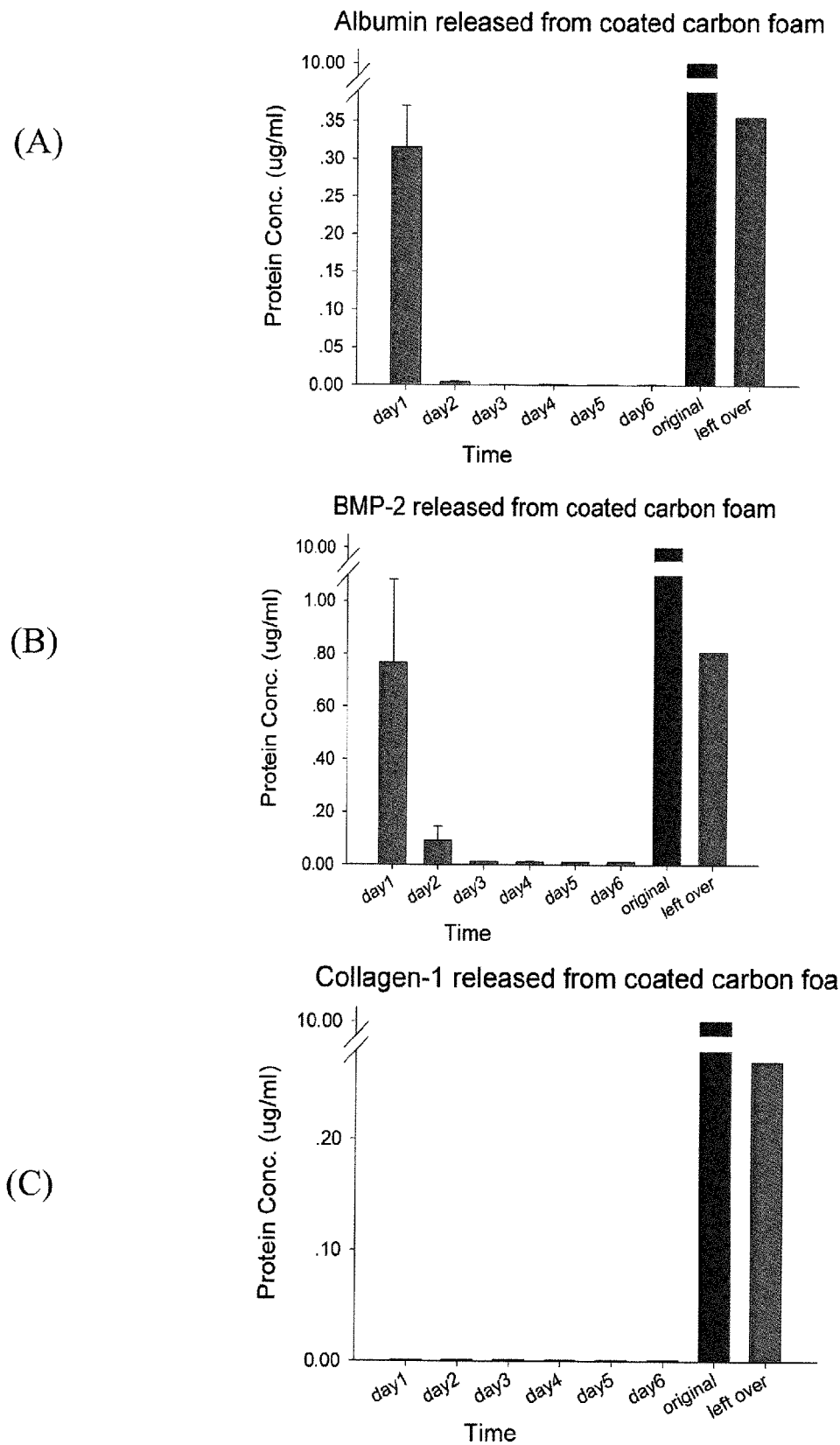
FIG. 16(A)-(C) shows charts for protein release assays from Example 5.

Both albumin and BMP-2 exhibited a minimal burst release in the first 24 hours with the albumin and BMP-2 releasing 0.108% and 0.2733%, respectively (FIG. 16A-B). These burst releases were followed by significantly reduced release rates thereafter. Collagen type I did not exhibit the same burst release profile as seen with albumin and BMP-2 in the first 24 hours (FIG. 16C). Collagen type I was released steadily at the rate of 0.0003% during 6 days of assessment. This negligible release of collagen type I from the carbon foam allowed a high retention of protein on the surface of the biomaterial, which subsequently contributed to its biological effect on attached cells. While the cumulative releases of albumin and BMP-2 from carbon were more than that of the collagen type I, the retentions of albumin and BMP-2 still were up to 99.89% and 99.68%, respectively. Therefore, it is possible that the minimal release rates have allowed sufficient amounts of albumin and BMP-2 to remain, and then sustain cell adhesion, proliferation, and the formation of bony matrix afterward. The stable and long retention of protein on the scaffold will allow for the increase of release duration and the local protein concentration. This pattern of release may rarely lead to a distant spread of the protein, and subsequent ectopic bone formation.

TABLE 2

Protein release from coated carbon foam

| | Albumin | | BMP-2 | | Collagen type I | |
|---|---|---|---|---|---|---|
| | Concentration (μg/ml) | Rate (%) | Concentration (μg/ml) | Rate (%) | Concentration (μg/ml) | Rate (%) |
| Day 1 | 0.31510 ± 0.05510 | 0.1081 | 0.76700 ± 0.31370 | 0.2733 | 0.00074 ± 0.00002 | 0.0003 |
| Day 2 | 0.00442 ± 0.00122 | 0.0015 | 0.09230 ± 0.05300 | 0.0329 | 0.00074 ± 0.00005 | 0.0003 |
| Day 3 | 0.00061 ± 0.00007 | 0.0002 | 0.01080 ± 0.00105 | 0.0038 | 0.00071 ± 0.00001 | 0.0002 |
| Day 4 | 0.00084 ± 0.00008 | 0.0003 | 0.01100 ± 0.00118 | 0.0039 | 0.00069 ± 0.00002 | 0.0002 |
| Day 5 | 0.00070 ± 0.00002 | 0.0002 | 0.01020 ± 0.00082 | 0.0036 | 0.00069 ± 0.00003 | 0.0002 |
| Day 6 | 0.00076 ± 0.00010 | 0.0003 | 0.00957 ± 0.00025 | 0.0034 | 0.00072 ± 0.00004 | 0.0002 |
| Original | 10.00000 | | 10.00000 | | 10.00000 | |
| Left over | 0.35570 | | 0.80780 | | 0.26970 | |

The percent release of protein at each time point was determined as follows:

$$\text{Release Rate} = \frac{\text{amount of protein released at day } X}{(50 \ \mu g \ \text{protein} - \text{amount of protein left over})/6 \ \text{samples}} \times 100\%$$

b. Osteoblast Characterization

Figure 17:
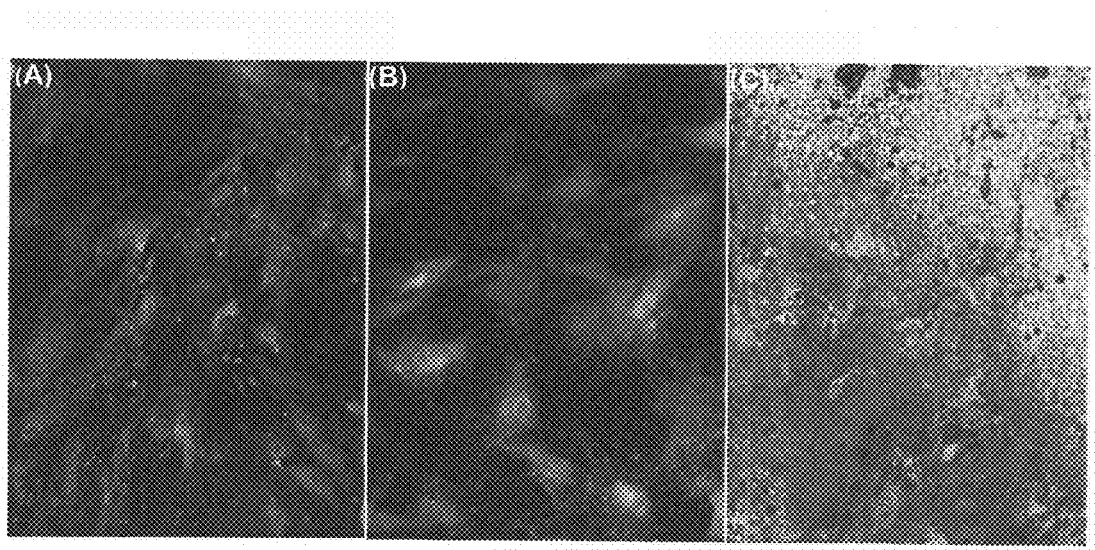
FIG. 17 shows images from the immunocytofluorescence test in Example 5.

The capacity of the induced osteoblasts to express osteocalcin, osteopontin, and collagen type I was examined by immunocytofluorescence (FIG. 17). While the expression of osteocalcin (in red, FIG. 17A) and osteopontin (in red, FIG. 17B) was prominent in the induced osteoblasts, these cells were further identified by positive staining for collagen type I (in green, FIG. 17A-B), indicating that the induced cells possessed the distinguishable osteoblastic phenotype. To demonstrate the ability of cells to mineralize the matrix, cells cultured on Petri dishes were subjected to von Kossa staining to reveal calcium deposition (FIG. 17C). The darkly stained mineralized nodules were visualized by silver nitrate, indicating normal osteoblast function in conditioned culture.

expression are functional and maturational indicators of the osteoblast phenotype, and partially correlated with capacity of bone formation. It seemed that the ALP activity responded to varying materials in a similar way to cell viability, with the higher values for ALP observed at the groups of collagen type I and $H_2O$. Compared with the other groups, the collagen type I stimulated higher osteocalcin expression, although the statistical significances were obscure with the exception of collagen type I vs. $H_2O$. BMP-2, the well-known osteogenic protein which has been widely used in bone reconstructive surgery, was expected to facilitate the osteoblast differentiation and function. In the current study, however, BMP-2 appeared not to provide a more favorable environment for osteoblast function, which was observed as the lower production of ALP and osteocalcin. Paradoxically, collagen type I and BMP-2 treated carbon foam led to an apparent cytotoxicity, which was indicated by a higher reading of the LDH ratio. It is difficult to interpret the concurrent promoting and inhibiting effect of collagen type I on the osteoblasts, which were evidenced by the higher readings in the alamarBlue® and LDH assays. The albumin group, however, exhibited the lowest cell viability (i.e., alamarBlue®/DNA) as well as the lowest adverse effect on the cells (i.e., LDH). In contrast,

TABLE 3

Cell culture on carbon foam

| | alamarBlue ® (OD/ug DNA) | ALP (OD/ug DNA) | Osteocalcin(ng/ug DNA) | LDH |
|---|---|---|---|---|
| Albumin | 0.007 ± 0.003 | 0.005 ± 0.003 | 0.039 ± 0.023 | −0.951 ± 1.041 |
| BMP-2 | 0.010 ± 0.001 | 0.006 ± 0.002 | 0.028 ± 0.011 | 1.491 ± 1.126 |
| Collagen I | 0.015 ± 0.001 | 0.008 ± 0.003 | 0.065 ± 0.045 | 1.829 ± 1.961 |
| $H_2O$ | 0.015 ± 0.002 | 0.009 ± 0.002 | 0.018 ± 0.013 | 0.520 ± 0.786 |

Figure 18:
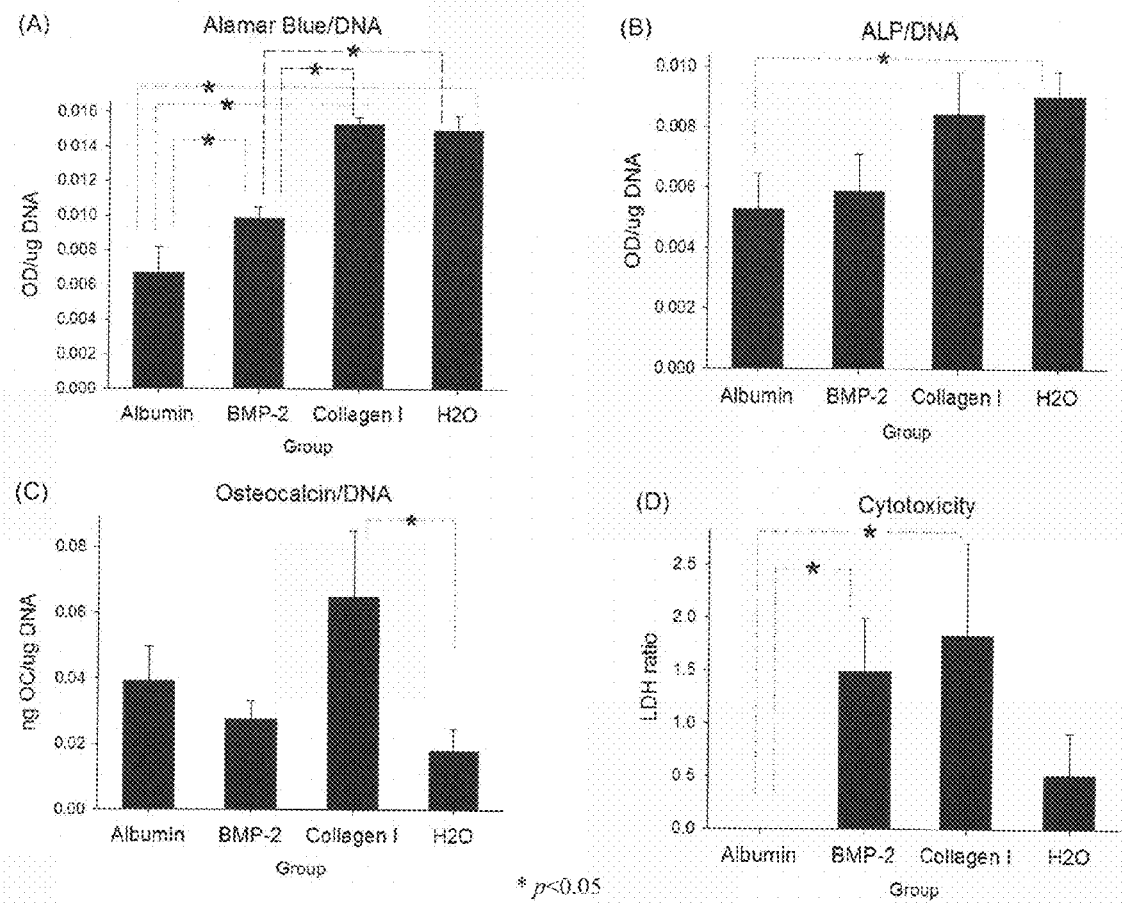
FIG. 18 shows charts for the effects of different protein coatings on osteoblasts from Example 5.
Figure 19:
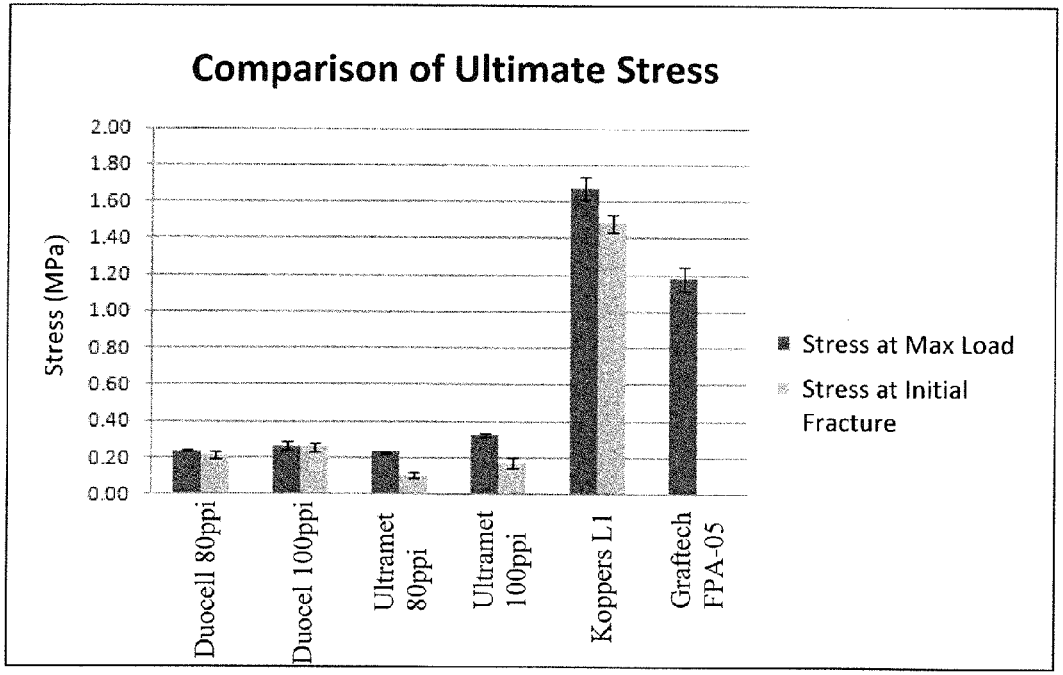
FIG. 19 is a comparison of the ultimate stress for the carbon foams tested in Example 6.
Figure 20:
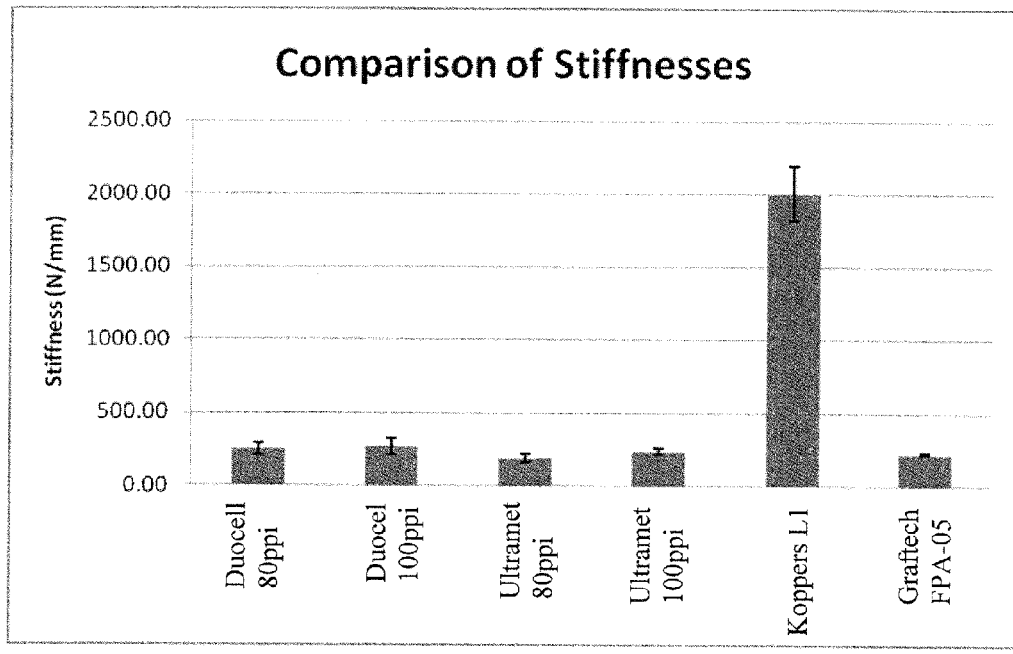
FIG. 20 is a comparison of the stiffness for the carbon foams tested in Example 6.
Figure 21:
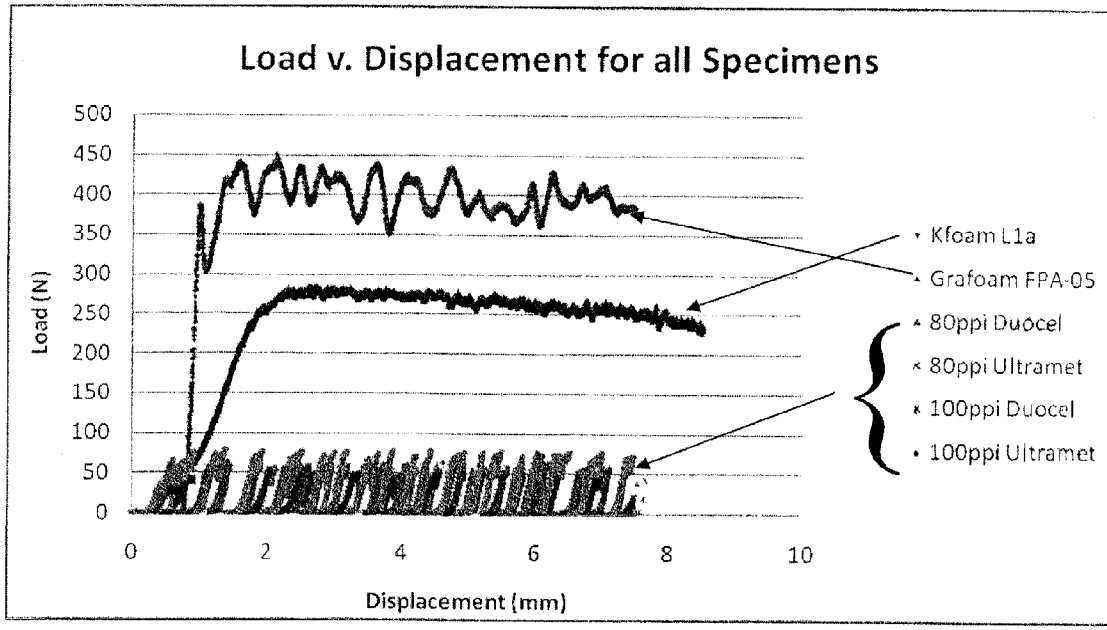
FIG. 21 is a graph of the load vs. displacement for all carbon foams tested in Example 6.
Figure 22:
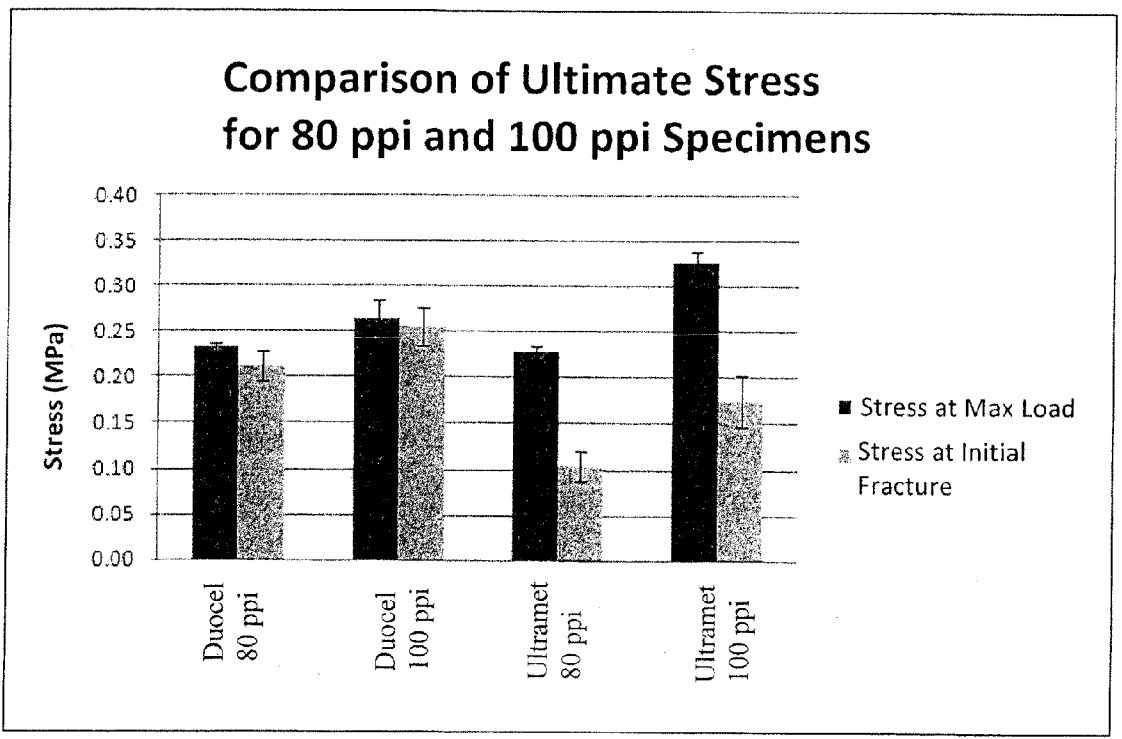
FIG. 22 is a graph comparing the ultimate stress of the 80 PPI and 100 PPI carbon foams from Example 6.
Figure 23:
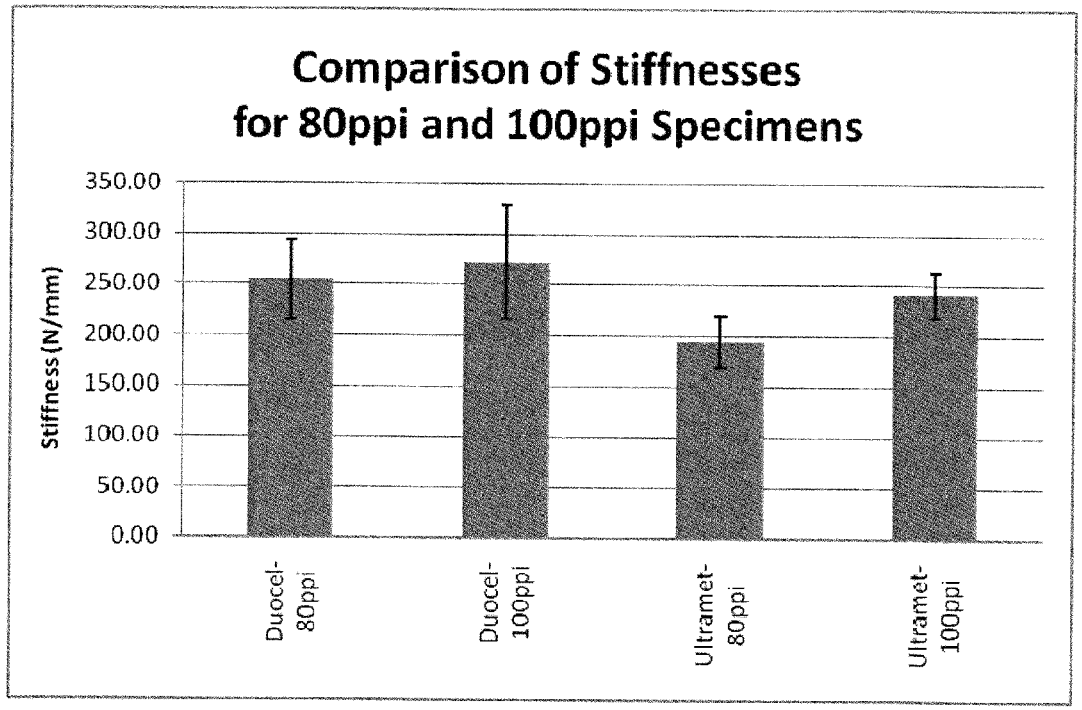
FIG. 23 is a graph comparing the stiffness of the 80 PPI and 100 PPI carbon foams from Example 6.
Figure 24A:
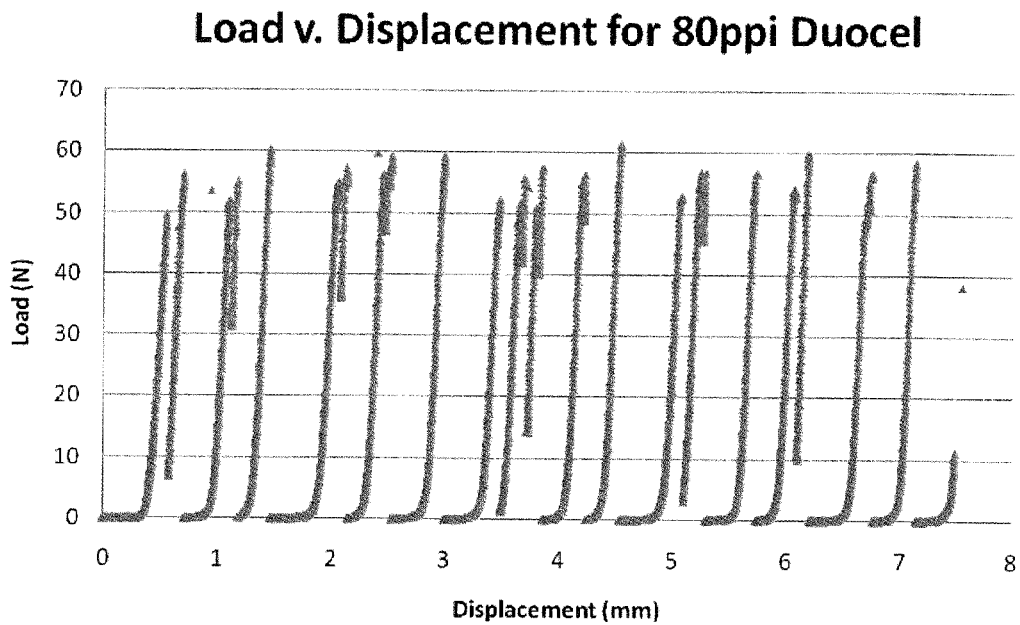
FIG. 24(A)-(B) are graphs of the load vs. displacement for the 80 PPI carbon foams in Example 6.
Figure 24B:
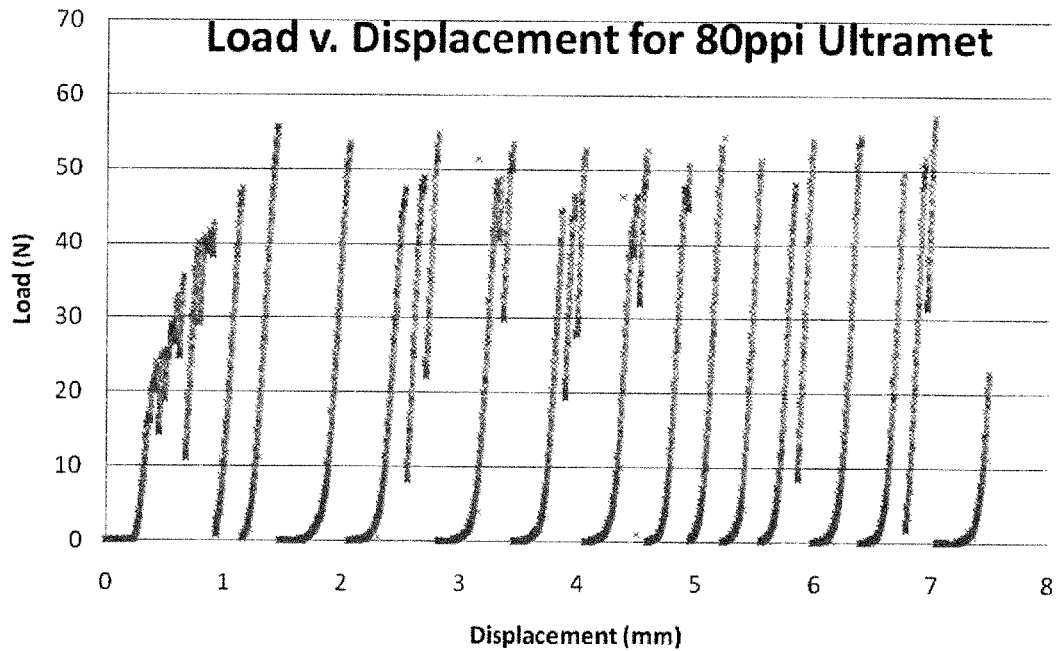
Figure 25A:
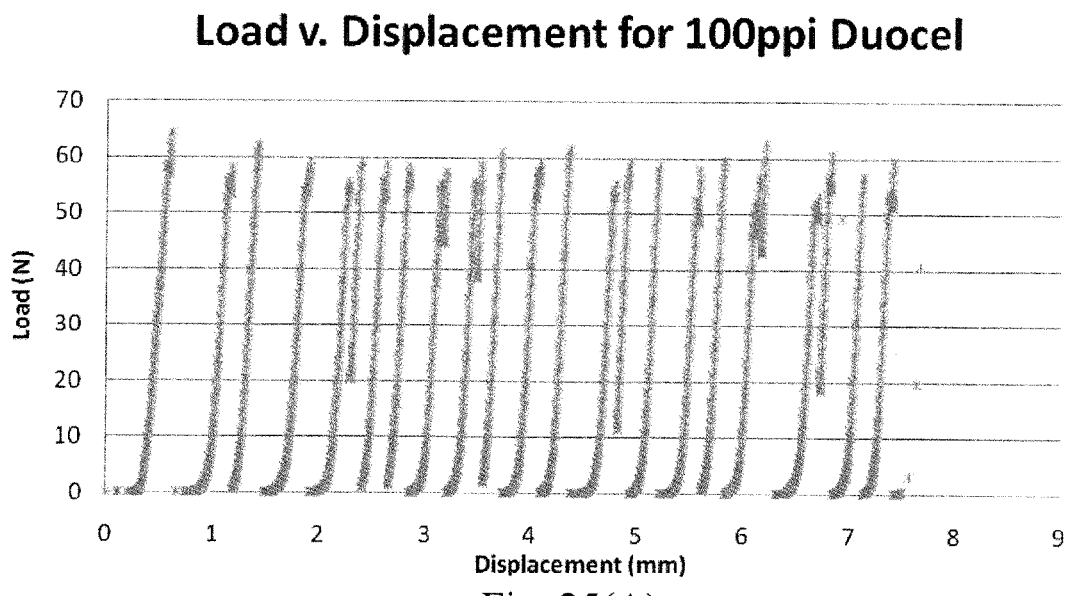
FIG. 25(A)-(B) are graphs of the load vs. displacement for the 100 PPI carbon foams in Example 6.
Figure 25B:
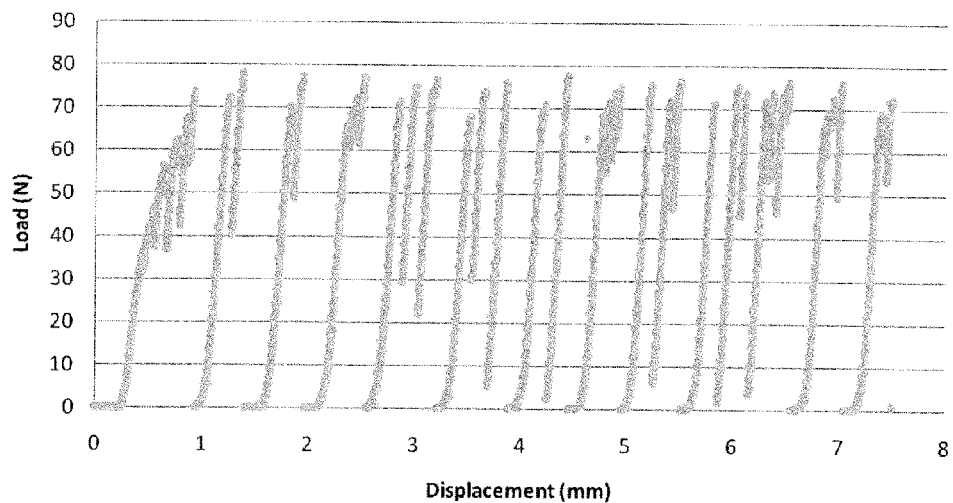
Figure 26:
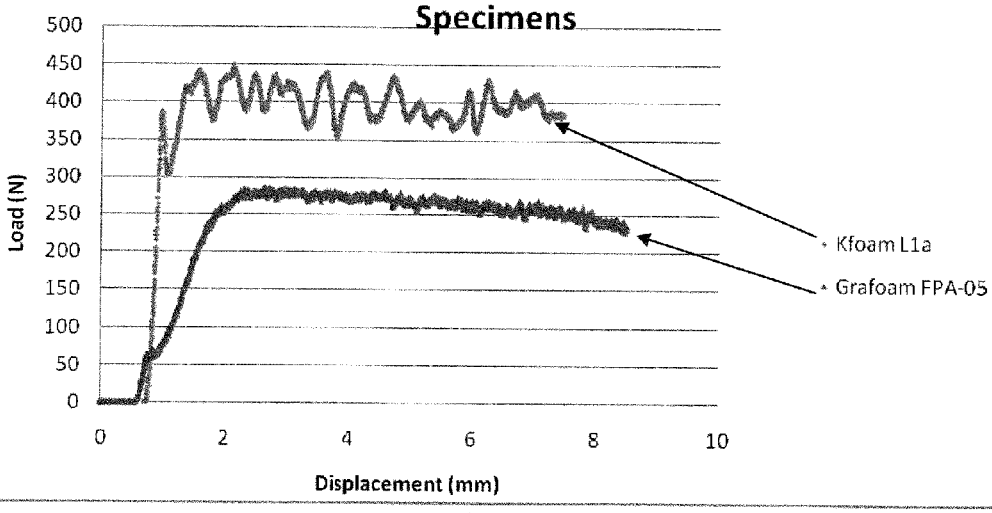
FIG. 26 is a graph of the load vs. displacement for the graphitic carbon foams in Example 6.

To test the effects of different protein coatings on osteoblasts, we analyzed cell viability, ALP activity, osteocalcin expression, and cell damage of osteoblasts using spectrophotometry or spectrofluorometry at the single-cell level by culturing cells on carbon foam in vitro for 1 week. Relative quantification of activities at the single-cell level was employed in this study, because augmented cellular functions and viabilities should definitely be pursued when cell amounts could be controlled relatively easily as assembling engineered bone. Comparisons were made among the groups of albumin, BMP-2, collagen type I, and $H_2O$ treated carbon foams (FIG. 18).

Collagen type I and $H_2O$ treated carbon foams led to higher cell viability than the albumin and BMP-2 groups, which were represented by the alamarBlue® reading normalized by DNA amount in each group. ALP activity and osteocalcin $H_2O$-treated carbon foam, with the absence of any protein coating, demonstrated promising properties: higher cell viability, lower cell toxicity, and higher ALP activity, with the exception of the lower osteocalcin production.

Example 6

Carbon Foam Biomechanical Testing

In this Example, several different carbon foam materials were tested (6 specimens of each): DUOCEL® 80 PPI; DUOCEL® 100 PPI; Ultramet 80 PPI RVC; Ultramet 100 PPI RVC; KFOAM® L1; and GRAFOAM® FPA-05. The data shown in the figures and table discussed below are based on a displacement driven compression test on six test specimens. Each of the graphs shown are from individual test data chosen as representative for each type of material (they are not based on test values averaged over all six specimens). The dimensions of the test species are indicated in the table below.

TABLE 4

Specimens for Mechanical Testing

| | specimen thickness | quantity | minimum | ordered |
|---|---|---|---|---|
| Elliptical cylinder major diam: 24 mm minor diam: 22 mm | 12 mm | 20 | 5" × 5" | 6" × 6" × 12 mm (×2) |
| | 15 mm | 20 | 5" × 5" | 6" × 6" × 15 mm (×2) |
| | 18 mm | 20 | 5" × 5" | 6" × 6" × 18 mm (×2) |

1. Results

The results are shown in the Table below, as well as in FIGS. 19-26, discussed in more detail below.

TABLE 5

Mechanical properties of each material tested (n = 6)

| Material | Stress at Max Load (MPa) | Stress at Initial Fracture (MPa) | Stiffness (N/m) |
|---|---|---|---|
| DUOCEL ® 80 PPI | 0.23 | 0.21 | 255.07 |
| DUOCEL ® 100 PPI | 0.26 | 0.26 | 272.97 |
| Ultramet 80 PPI RVC | 0.23 | 0.10 | 194.27 |
| Ultramet 100 PPI RVC | 0.33 | 0.18 | 241.22 |
| KFOAM ® L1 | 1.68 | 1.49 | 2006.67 |
| GRAFOAM ® FPA-05 | 1.19 | 0 | 226.65 | a. Biomechanical Observations

The strength of KFOAM® L1 foam was the greatest, with the GRAFOAM® FPA-05 coming in second. Both of these foams were much more dense and closed-celled than the DUOCEL® and Ultramet foams tested. Of the L1 and FPA-05, the latter had a more open pored structure. Both 80 PPI foams had approximately the same stress at maximum load, but the Ultramet 100 PPI foam could withstand a greater stress than the DUOCEL®. Both DUOCEL® foams reached a higher stress value before initial fracture than did the Ultramet foams, with both of the initial fractures for the Ultramet foams coming at close to half of their stress at their maximum load.

b. Stiffnesses

The stiffnesses for both of the DUOCEL® foams were greater than their respective Ultramet partners. GRAFOAM® FPA-05's stiffness was similar to the 80 and 100 PPI foams although its maximum stress value was much higher. The stiffness of the KFOAM® L1 was much higher than any of the other material types, although its standard deviation was also much greater (187.77).

c. Load vs. Displacement Curves

The load vs. displacement curves shown are created from data taken from individual tests which were chosen to represent the general curves seen for the other five specimens. The DUOCEL® and Ultramet foams were tested in-house using the Bose ElectroForce 3200. The KFOAM® and GRAFOAM® specimens were tested at ORI on the MTS Bionix testing system. Because of the differences in force production methods, the graphs are shaped differently. The MTS system delivered displacement rates as it should while the Bose system would overshoot when fractures occurred. Because of this overshooting, the machine would back the plate up to the position that it should have been in and then continue moving forward from that point. This can be seen in the Load vs. Displacement graphs in the material data sheets when the data points before they were sampled are connected by lines.

2. Conclusions

The maximum stress for the DUOCEL® 80 PPI foam is very similar to the Ultramet 80 PPI foam, but its stress at initial fracture is higher than that of the Ultramet 80 PPI foam. The DUOCEL® 100 PPI foam has a lower maximum strength than the Ultramet, but it also has a higher initial fracture stress. The stiffnesses for both DUOCEL® foams are also greater than both of the Ultramet foams.

The Ultramet foams have similar maximum stress values to their respective DUOCEL® foams, but have decreased initial fracture stresses. Their stiffnesses are less than the DUOCEL® foams. They are also more expensive than the DUOCEL® foams.

The strength of the KFOAM® foam was the greatest of all of the material types tested. The Stiffness was also by far the greatest of all the specimen types, by nearly 10×. The standard deviation of the stiffness for this foam is also the largest (SD ~188) as compared to the second largest—DUOCEL® 100 PPI (SD~56).

While the strength of the GRAFOAM® graphitic foam was much larger than the DUOCEL® and Ultramet foams tested and was somewhat less than the KFOAM® foam, the stiffness was nearly the same as the DUOCEL® and Ultramet foams, all being nearly 10× less than that of the KFOAM® foam. While being loaded this foam initially has a specific stiffness. It then realigns and continues with a lower stiffness value up until its first major failure value, a trait which no other foam type exhibits.

Example 7

BMP-2 Adsorption, Release and Osteoinduction

In this Example, the ability of carbon foam materials to deliver BMP-2 to mesenchymal stem cells in a form promotive of osteoblast differentiation was studied. These initial tests examine two interrelated aspects: quantitative aspects of BMP-2 binding to two carbon foam materials using an ELISA assay; and verification of cytokine binding through ELISA analysis of the amount of presumptive bound cytokine desorbed using chemical means. A preliminary account of stem cell replication and osteoinduction is also presented. DUOCEL® 80 PPI vitreous carbon foam and Kopper KFOAM® 80 PPI graphitic carbon foam was used. The specimens were cut from manufacturer's blocks using biopsy punches into cylinders, 8-10 mm in diameter and 2-3 mm in thickness, depending on test protocol (see below). Additional processing is described below.

1. BMP-2 Binding Assay

Carbon foam cylinders were sterilized by immersion in 70% ethanol for 4 hours followed by centrifugation to removed wicked liquid, then air dried in a laminar flow hood for 14 hr. BMP-2 solutions (10, 5 and 2 µg/ml) in sterile water were prepared and 1 ml of each solution was applied to carbon foam constructs in a 12-well cell culture plate. Plates were transferred to a vacuum apparatus at 37° C. and the BMP solution was driven into the foam void volume in vacuo for 24 hr. Excess BMP solution was then removed from the cylinders by centrifugation for 5 min. at 200 rpm and the foams were transferred to clean wells and air dried over night. The BMP wash solutions (original soak plus 200 rpm void volume fraction) were combined and stored at −20° C. for ELISA estimation of unbound BMP-2 (i.e., "left over" fraction not absorbed by the foam). The dried carbon discs were then taken through 6 cycles of rinsing (by immersion) in 1 ml PBS followed by centrifugation, pooling of eluates, and drying ("days 1-6 eluates"). ELISA assays of BMP-2 standards, soak solutions, post-soak solutions and disc rinses were performed using a sandwich assay. Standard curves were generated using the same commercial BMP-2 product used for binding (eBioscience).

2. BMP-2 Elution Assay

Carbon foam discs were pre-absorbed in stock BMP-2 solutions (2 μg/ml) using low pressure vacuum as described above. Hydrated discs were then centrifuged at 200 rpm as above and the removed liquid combined with the original soak solution. This step was followed by two 24-hr PBS rinses conducted as described above. The rinsed BMP-infused discs were then subjected to two separate elution regimes consisting of a 4 hr soak in 1M glycine or a 2 hr soak in 4M guanidine hydrochloride. These solutions are routinely used to solubilize adsorbed, immobilized proteins or proteins embedded in an extracellular matrix. The eluate solutions were combined with liquid expressed by 200 rpm centrifugation and neutralized by the addition of 72 μM Tris to effect a shift to pH 7.5. The neutralized eluate solutions along with control BMP-2 solutions containing glycine or guanidine salts at concentrations equivalent to experimental discs were analyzed by ELISA as described above.

3. C2C12 Replication and Osteoblast Induction Assays

Both types of carbon foam discs were ethanol sterilized, wet in PBS and then PBS containing 100 ng BMP-2 was applied directly to the materials. The BMP was allowed to adsorb to the materials for 2 hr at 37° C. Ten thousand C2C12 mouse myoblast cells were then added to empty wells (tissue culture polystyrene) or applied (in a volume of 50 μl) to carbon foam discs with and without preadsorbed BMP. Following a 2 hr attachment of cells at 37° C., all wells received 400 μl DMEM tissue culture medium+10% FBS. At days 1, 3, 5 and 7 post-plating, wells containing the complete data set were processed for MTT and alkaline phosphatase activity assays.

4. Results a. BMP-2 Binding Assay

Figure 27:
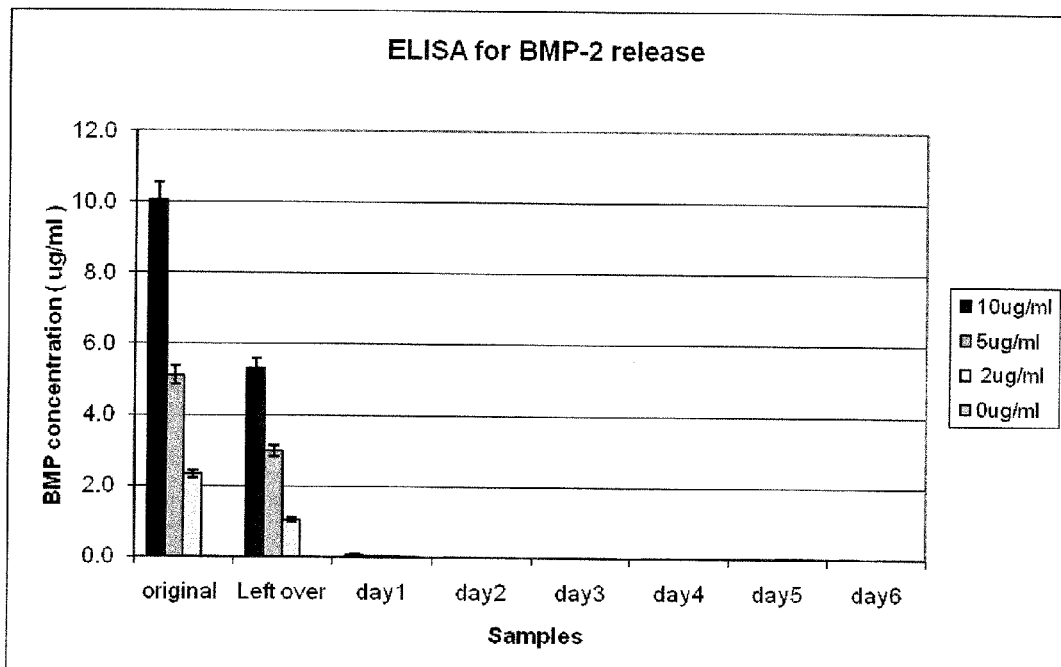
FIG. 27 is a graph of BMP concentration in test soak solutions ("original"), and post-soak ("left over") solutions as well as subsequent Days 1-6 with PBS wash solutions from Example 7.
Figure 28:
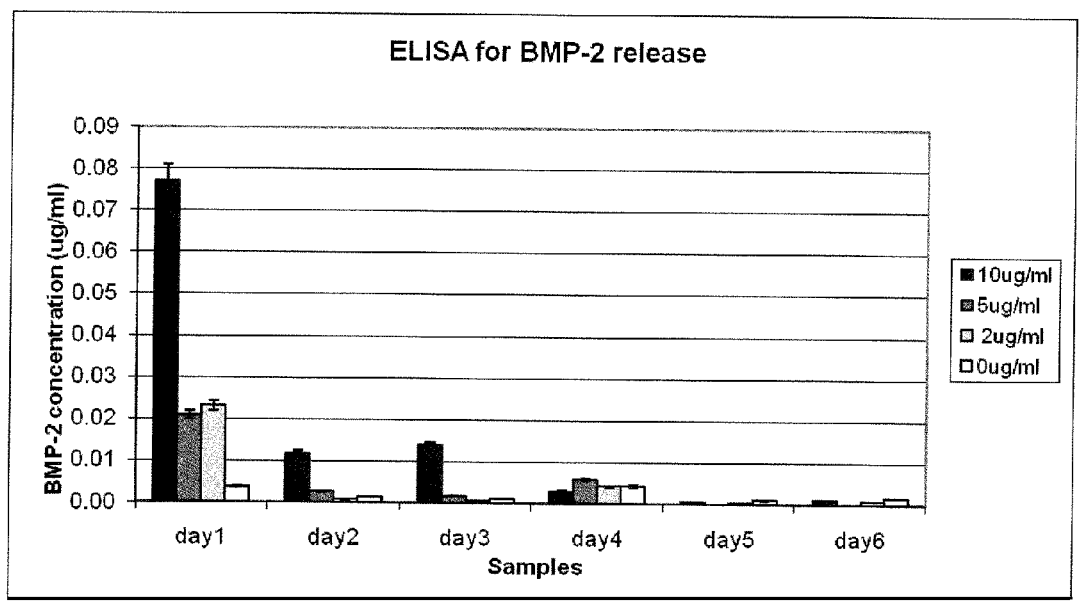
FIG. 28 is a graph of BMP concentration from Days 1-6 PBS wash solutions in Example 7.

The initial binding assay revealed that approximately one half (~50%) of the BMP-2 in the soak solution was recovered following the 24 hr exposure to carbon foam (FIG. 27). This result was obtained irrespective of the starting concentration of the BMP-2 stock solution. More precisely, the concentration of the soak solutions was decreased approximately 50% following carbon disc exposure. Significantly, additional PBS rinses designed to elute loosely bound BMP protein or entrapped BM BMP solution resulted in only small incremental detection of released BMP by ELISA over a 6 day period (FIG. 28). The amount of BMP-2 released from each BMP soak concentration amounted only to approximately 1% of the input total.

b. BMP-2 Elution Assay

The results of the BMP-2 elution assays using guanidine-HCl and glycine chaotropes were inconclusive. In both cases preadsorption of BMP-2 at a concentration of 2 μg/ml in the soak solution yielded approximately 50% loading of cytokine onto the material and 50% presumably bound to carbon. BMP-2 was not detected in either desorption solution suggesting that either some proportion of BMP-2 in the soak contacts carbon and is denatured (rendering the cytokine undetectable by BMP IgG in the ELISA) or that BMP is indeed bound but irreversibly so.

c. C2C12 Cell Replication and Alkaline Phosphatase Induction Assays

We have been interested in establishing baseline data for cell replication and osteoblastic phenotype development in response to contact with carbon foam materials. We incorporated BMP in these studies as a positive control for osteoblast marker induction as well as to determine if synergy with carbon materials (positive of negative) was taking place. This preliminary study included one representative each of the vitreous (DUOCEL®) and graphitic (KFOAM®) carbon materials. C2C12 myoblasts were chosen for these preliminary assays owing to their multipotent capabilities including osteoblast phenotypic acquisition.

Figure 29:
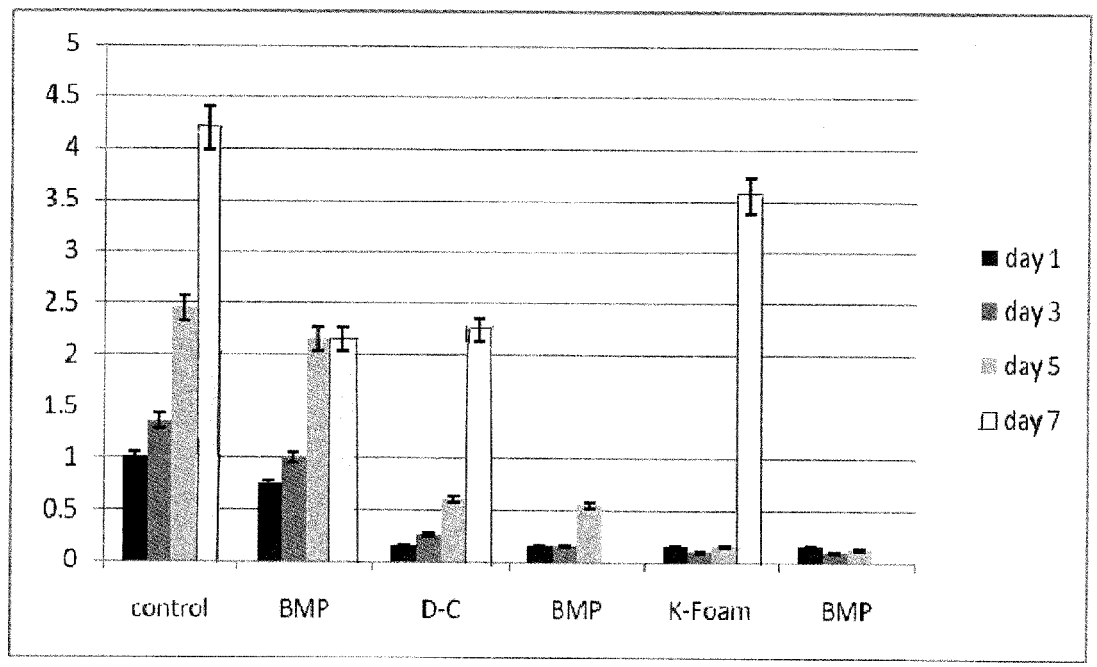
FIG. 29 is a graph of data for triplicate cell cultures over a 7 day interval of the relative cell replication in TCP and on carbon foams (+/−200 ng/ml BMP), with data normalized with respect to control (−BMP, no carbon foam) wells (arbitrarily set at 1) from Example 7.

Replication of C2C12 cells was determined using a standard MTT assay that measures cell respiration. Relative numbers of cells among treatment wells can thereby be fairly accurately determined. In these studies cell number was found to increase with increasing time in culture, as anticipated. At any given time point the number of cells in the TCP wells exceeded the numbers in culture of cells applied to either carbon foam (FIG. 29). Significantly, perhaps, a lag in cell number in the carbon foam cultures was seen but not in the TCP wells. Consistent with the literature of differentiating pluripotent stem cells, BMP at a concentration of 200 ng/ml reduced cell replication below untreated controls for all treatments. BMP+foam exposure proved to be cytotoxic since cell numbers approached 0 by day 7 by the criteria imposed by the MTT assay.

Figure 30:
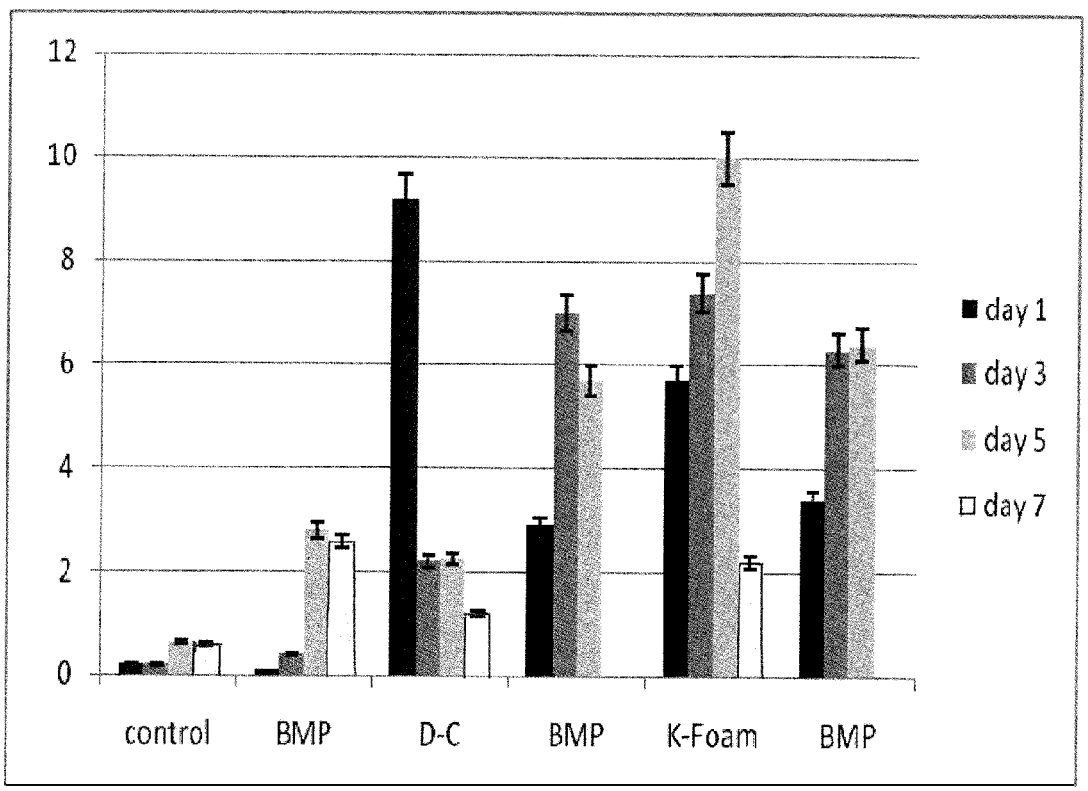
FIG. 30 is a graph of data for triplicate cell cultures over a 7-day interval of alkaline phosphatase activity (delta OD406/min) for control and foam-exposed cells, +/−200 ng/ml BMP from Example 7.

Alkaline phosphatase is a key enzyme induced early in the cycle of events leading to osteoblast differentiation. Levels of this enzyme activity are close to 0 in unstimulated C2C12 cells, with induction by BMP occurring rapidly, within a day or two of cytokine exposure. Consistent with this dogma AlkPhos was indeed provoked by BMP in control cell cultures between days 3 and 5 (FIG. 30). Interestingly, AlkPhos activity in cells exposed to both carbon foams in the absence of BMP increased circa 5- to 50-fold by day 3. For DUOCEL® vitreous carbon an additional 2-3-fold increment of activity was provoked by BMP. This cytokine-synergistic effect was not observed for graphitic KFOAM®. Consistent with the MTT viability results, AlkPhos activity was undetectable in day 7 cultures where cell numbers had declined in the MTT assay (compare FIG. 29).

5. Conclusions

We were somewhat surprised by the lack of BMP elution detected from rinsed, preloaded carbon discs since protein binding by several forms of carbon materials is strong (but not covalent) and can be irreversible. It is likely that the tightly bound BMP retains biological activity based upon the alkaline phosphatase induction results. The C2C12 cells tested exhibited relatively good biocompatibility in contact with the vitreous and graphitic foams. Replication, viability and inductivity were maintained for at least 5 days in culture. The decrement in these parameters at day 7 are likely due to poor material penetration of nutrients and/or oxygen which owing to neovascularization seen in these materials in previous animal studies, should not be a problem in vivo. We were somewhat surprised to see osteoinductivity exhibited by the foams in the absence of BMP. This important property has been observed in other non-biologic implant materials as well. This property, in combination with positive synergy seen with BMP-2 may well prove to be decisive for providing a novel bone bridging, void filling material for the orthopedic community.

We claim:

1. A porous, self-sustaining body useful as a scaffold for bone grafting in a subject comprising:
   a carbonaceous matrix formed of vitreous carbon foam, said matrix comprising a continuous phase having a surface and defining a plurality of open spaces throughout said matrix, wherein said open spaces comprise pores in said matrix, said matrix having an average pore diameter of at least 50 μm and a porosity of at least 80%; and
   a coating immobilized and adsorbed on said continuous phase surface of said matrix, said coating being selected from the group consisting of osteogenic materials, therapeutic agents, and combinations thereof, wherein said osteogenic materials and/or therapeutic agents are tightly bound to said carbonaceous matrix and retain their bioavailability after implantation in said subject, wherein said osteogenic materials and/or therapeutic agents are retained by said matrix at the site of implantation;
   wherein said porous body is substantially free of metals.

2. The porous, self-sustaining body of claim 1, wherein said carbonaceous matrix comprises an open cell structure having a plurality of interconnected pores throughout said matrix.

3. The porous, self-sustaining body of claim 1, wherein said carbonaceous matrix has a pore density of at least about 50 PPI.

4. The porous, self-sustaining body of claim 1, wherein said porous, self-sustaining body has a ultimate compressive stress of from about 0.2 to about 15 MPa.

5. The porous, self-sustaining body of claim 1, wherein said porous, self-sustaining body is readily shapeable.

6. The porous, self-sustaining body of claim 1, wherein said carbonaceous matrix is substantially of a uniform material throughout said matrix.

7. The porous, self-sustaining body of claim 1, wherein said porous body is substantially free of inorganic materials.

8. The porous, self-sustaining body of claim 1, wherein at least about 75% of said continuous phase surface is covered by said coating.

9. The porous, self-sustaining body of claim 1, wherein said coating is an osteogenic material or therapeutic agent selected from the group consisting of osteoconductive materials, osteoinductive materials, biologics, and combinations thereof.

10. The porous, self-sustaining body of claim 1, wherein said coating is an osteogenic material or therapeutic agent selected from the group consisting of bone fragments, calcium phosphate, hydroxyapatite, corallin, sintered bone, porous polycaprolactone, antibiotics, anti-inflammatories, anti-coagulants, proteins, monoclonal antibodies, immunoglobulins, fusion proteins, cells, subcellular fractions, tissues, whole blood, blood components, enzymes, DNA, cDNA, gene therapy vectors, nucleic acid inhibitors, chemotherapeutics, and combinations thereof.

11. The porous, self-sustaining body of claim 1, wherein said porous body consists essentially of said carbonaceous matrix and said coating.

12. The porous, self-sustaining body of claim 1, wherein said porous body retains at least about 75% of the immobilized osteogenic materials and/or therapeutic agents, when subjected to a protein release test.

13. The porous, self-sustaining body of claim 1, wherein said osteogenic materials and/or therapeutic agents are proteins, and wherein said porous body after implantation retains at least about 75% of said protein, based upon the total initial protein content of the coating before implantation taken as 100%.

14. A method of making a porous, self-sustaining body useful as a scaffold for bone grafting, said method comprising:
   providing a carbonaceous matrix formed of vitreous carbon foam, said matrix comprising a continuous phase having a surface and defining a plurality of open spaces throughout said matrix, wherein said open spaces comprise pores in said matrix, said matrix having an average pore diameter of at least 50 μm and a porosity of at least 80%; and
   forming a coating adjacent said continuous phase surface of said matrix, said coating immobilized and adsorbed on said continuous phase surface of said matrix, said coating being selected from the group consisting of osteogenic materials, therapeutic agents, and combinations thereof, wherein said osteogenic materials and/or therapeutic agents are tightly bound to said carbonaceous matrix and retain their bioavailability after implantation in said subject, wherein said osteogenic materials and/or therapeutic agents are retained by said matrix at the site of implantation;
   wherein said porous body is substantially free of metals.

15. The method of claim 14, wherein said forming is selected from the group consisting of plasma deposition, immersion, spraying, puddling, vacuum pressure, and combinations thereof.

16. The method of claim 14, wherein said coating is a protein, said coating being formed by:
   immersing said matrix into a solution comprising said protein, said solution having an initial protein content; and
   removing said matrix from said solution,
   wherein after said immersing and removing, at least about 50% of said initial protein content is removed from said solution by said matrix.

17. The method of claim 16, said coating comprising a first amount of protein, wherein said matrix when subjected to a protein release test for a period of about a week, retains at least about 75% of said first amount of protein.

18. A method of repairing or replacing in a subject a bone void having a given size and shape comprising:
   providing a porous, self-sustaining body according to claim 1;
   shaping said porous body to substantially fit said bone void size and shape; and
   implanting said porous body into said subject, said implanting comprising fitting said porous body into said bone void.

19. The method of claim 18, wherein said shaping is selected from the group consisting of cutting, carving, shaving, slicing, grinding, boring, sanding, and combinations thereof.

20. The method of claim 18, further comprising further shaping said porous body after said fitting.

21. The method of claim 18, wherein said bone void is in a limb of said subject, wherein said subject returns to reduced ambulatory weight-bearing within less than about 4 days after said implanting.

22. The method of claim 18, wherein said porous body is at least about 75% resorbed about 6 weeks after said implanting.

23. A kit for use in repairing or replacing in a subject a bone void having a given size and shape, said kit comprising:
   porous, self-sustaining body useful as a scaffold for bone grafting, said porous body comprising:

a carbonaceous matrix formed of vitreous carbon foam, said matrix comprising a continuous phase having a surface and defining a plurality of open spaces throughout said matrix, wherein said open spaces comprise pores in said matrix, said matrix having an average pore diameter of at least 50 μm and a porosity of at least 80%; and a coating immobilized and adsorbed on said continuous phase surface of said matrix, said coating being selected from the group consisting of osteogenic materials, therapeutic agents, and combinations thereof, wherein said osteogenic materials and/or therapeutic agents are tightly bound to said carbonaceous matrix and retain their bioavailability after implantation in said subject, wherein said osteogenic materials and/or therapeutic agents are retained by said matrix at the site of implantation, and wherein said porous body is substantially free of metals; and instructions for the implantation thereof into said subject.

24. The kit of claim 23, further comprising:

instructions for shaping said porous, self-sustaining body to substantially fit the size and shape of said bone void; and optionally, one or more tools for the shaping thereof.

25. The kit of claim 23, wherein said porous body retains at least about 75% of the immobilized osteogenic materials and/or therapeutic agents, when subjected to a protein release test.

26. The kit of claim 23, wherein said osteogenic materials and/or therapeutic agents are proteins, and wherein said porous body after implantation retains at least about 75% of said protein, based upon the total initial protein content of the coating before implantation taken as 100%.

* * * * *